(12) United States Patent
Zitterbart et al.

(10) Patent No.: US 10,954,266 B2
(45) Date of Patent: Mar. 23, 2021

(54) LINKER MOLECULE AND USE THEREOF IN METHODS FOR PURIFYING PEPTIDES

(71) Applicant: BELYNTIC GMBH, Berlin (DE)

(72) Inventors: Robert Zitterbart, Berlin (DE); Oliver Seitz, Berlin (DE)

(73) Assignee: BELYNTIC GMBH, Berlin (DE)

( * ) Notice: Subject to any disclaimer, the term of this patent is extended or adjusted under 35 U.S.C. 154(b) by 0 days.

(21) Appl. No.: 16/073,794

(22) PCT Filed: Jan. 30, 2017

(86) PCT No.: PCT/EP2017/051932
§ 371 (c)(1),
(2) Date: Dec. 26, 2018

(87) PCT Pub. No.: WO2017/129818
PCT Pub. Date: Aug. 3, 2017

(65) Prior Publication Data
US 2019/0309013 A1    Oct. 10, 2019

(30) Foreign Application Priority Data

Jan. 29, 2016 (DE) .................. 10 2016 101 606.3

(51) Int. Cl.
| | | |
|---|---|---|
| *C07K 1/06* | (2006.01) | |
| *C07C 243/26* | (2006.01) | |
| *C07C 317/28* | (2006.01) | |
| *C07D 207/46* | (2006.01) | |
| *C07K 1/10* | (2006.01) | |
| *C07K 1/14* | (2006.01) | |
| *C07K 7/06* | (2006.01) | |
| *C07K 7/08* | (2006.01) | |
| *C07K 14/435* | (2006.01) | |
| *C07C 243/38* | (2006.01) | |
| *C07C 317/18* | (2006.01) | |
| *C07K 1/107* | (2006.01) | |

(52) U.S. Cl.
CPC ............ *C07K 1/061* (2013.01); *C07C 243/26* (2013.01); *C07C 243/38* (2013.01); *C07C 317/18* (2013.01); *C07C 317/28* (2013.01); *C07D 207/46* (2013.01); *C07K 1/10* (2013.01); *C07K 1/14* (2013.01); *C07K 7/06* (2013.01); *C07K 7/08* (2013.01); *C07K 14/435* (2013.01); *C07K 1/107* (2013.01)

(58) Field of Classification Search
CPC ... C07C 243/26; C07C 243/38; C07C 317/18; C07C 317/28; C07D 207/46; C07K 14/435; C07K 1/061; C07K 1/10; C07K 1/107; C07K 1/14; C07K 7/06; C07K 7/08
See application file for complete search history.

(56) References Cited

U.S. PATENT DOCUMENTS 8,597,631 B2 * 12/2013 Warnecke .............. A61K 47/60
424/78.17
2012/0270937 A1    10/2012 Warnecke et al.

FOREIGN PATENT DOCUMENTS

| EP | 0552368 | 7/1993 |
| EP | 2501711 | 1/2014 |
| WO | 01/31063 | 5/2001 |

* cited by examiner

*Primary Examiner* — Marcela M Cordero Garcia
(74) *Attorney, Agent, or Firm* — JMB Davis Ben-David

(57) ABSTRACT

The present invention relates to a method for the purification of peptides which are produced by solid phase peptide synthesis (SPPS) and corresponding linker molecules for use in said method.

14 Claims, 12 Drawing Sheets

Specification includes a Sequence Listing.

A

B

C

D

E

F

G

H (upper panel)

H (lower panel)

```
                       SEQUENCE LISTING

<160> NUMBER OF SEQ ID NOS: 10

<210> SEQ ID NO 1
<211> LENGTH: 8
<212> TYPE: PRT
<213> ORGANISM: Artificial Sequence
<220> FEATURE:
<223> OTHER INFORMATION: Peptide for the demonstration of the
      reversibility of the hydrazone bond with a purification resin

<400> SEQUENCE: 1

Gly Leu Tyr Ala Glu Gly Gly Gly
1               5

<210> SEQ ID NO 2
<211> LENGTH: 6
<212> TYPE: PRT
<213> ORGANISM: Artificial Sequence
<220> FEATURE:
<223> OTHER INFORMATION: Peptide for a native chemical ligation

<400> SEQUENCE: 2

Tyr Glu Asn Arg Ile Lys
1               5

<210> SEQ ID NO 3
<211> LENGTH: 12
<212> TYPE: PRT
<213> ORGANISM: Homo sapiens

<400> SEQUENCE: 3

Thr Leu Ala Asp Glu Val Ser Ala Ser Leu Ala Lys
1               5                   10

<210> SEQ ID NO 4
<211> LENGTH: 13
<212> TYPE: PRT
<213> ORGANISM: Homo sapiens

<400> SEQUENCE: 4

Ala Thr Leu Ala Asp Glu Val Ser Ala Ser Leu Ala Lys
1               5                   10

<210> SEQ ID NO 5
```

<211> LENGTH: 32
<212> TYPE: PRT
<213> ORGANISM: Homo sapiens

<400> SEQUENCE: 5

Cys Gln Trp Ser Leu His Arg Lys Arg His Leu Ala Arg Thr Leu Leu
1               5                   10                  15

Thr Ala Ala Arg Glu Pro Arg Pro Ala Pro Pro Ser Ser Asn Lys Val
            20                  25                  30

<210> SEQ ID NO 6
<211> LENGTH: 23
<212> TYPE: PRT
<213> ORGANISM: Homo sapiens

<400> SEQUENCE: 6

Gly Ile Gly Lys Phe Leu His Ser Ala Lys Lys Phe Gly Lys Ala Phe
1               5                   10                  15

Val Gly Glu Ile Met Asn Ser
            20

<210> SEQ ID NO 7
<211> LENGTH: 9
<212> TYPE: PRT
<213> ORGANISM: Homo sapiens

<400> SEQUENCE: 7

Tyr Leu Phe Phe Tyr Arg Lys Ser Val
1               5

<210> SEQ ID NO 8
<211> LENGTH: 20
<212> TYPE: PRT
<213> ORGANISM: Homo sapiens

<400> SEQUENCE: 8

Phe Pro Arg Pro Gly Gly Gly Gly Asn Gly Asp Phe Glu Glu Ile Pro
1               5                   10                  15

Glu Glu Tyr Leu
            20

<210> SEQ ID NO 9
<211> LENGTH: 12
<212> TYPE: PRT
<213> ORGANISM: Homo sapiens

<400> SEQUENCE: 9

Gly Arg Lys Lys Arg Arg Gln Arg Arg Arg Pro Gln
1               5                   10

<210> SEQ ID NO 10
<211> LENGTH: 13
<212> TYPE: PRT
<213> ORGANISM: Artificial Sequence
<220> FEATURE:
<223> OTHER INFORMATION: Peptide for the demonstration of the
      regeneration of the aldehyde resin and purification experiments

<400> SEQUENCE: 10

Ala Lys Ala Asp Glu Val Ser Leu His Lys Trp Tyr Gly
1               5                   10

LINKER MOLECULE AND USE THEREOF IN METHODS FOR PURIFYING PEPTIDES

CROSS-REFERENCE TO RELATED APPLICATIONS

This is the U.S. National Stage of International Patent Application No. PCT/EP2017/051932 filed Jan. 30, 2017, which was published in German under PCT Article 21(2), and which in turn claims the benefit of German Patent Application No. 10 2016 101 606.3 filed Jan. 29, 2016.

FIELD OF THE INVENTION

The present invention relates to a method for the purification of peptides produced by solid phase peptide synthesis (SPPS) and corresponding linker molecules for use in this method.

BACKGROUND AND STATE OF THE ART

Solid phase peptide synthesis is a well-known method for the production of peptides. Apart from the synthesis of the peptides, their purification is also an essential process step.

A widely used method for the purification of peptides is the preparative high performance liquid chromatography (HPLC). Disadvantageous at this method is the poor scalability with regard to the desired production quantities, so that different quantities cannot be produced with one and the same system; this causes relatively high acquisition costs for the corresponding complex devices. A further disadvantage is that the correct analytical assessment of the individual fractions requires relatively extensive knowledge; additionally, there is the consumption of solvents and column material (solid phase) during operation.

Therefore, methods that are cheaper and less prone to faults would be advantageous for reducing the costs of peptide production.

EP 0 552 368 A1 describes a method for the purification of peptides in which a so-called linker is on the one hand covalently bound to the N-terminal end of the synthesized full-length peptide and on the other hand covalently bound by reaction to thioether of a thiol group with functionalized diatomaceous earth. The full-length peptide is thus immobilized and can be purified. The full-length peptide is then released under basic conditions. However, the method is not suitable for thiol-containing peptides such as those comprising the amino acid cysteine or penicillamine. Furthermore, there is the disadvantage that the solid phase used for purification (in this case diatomaceous earth) is not intended or suitable for reuse.

EP 2 501 711 B1 proposes an analogous method in which the linker is bound to a solid phase (synthetic hydrophilic polymer, e.g. PEGA) via the N-terminal end of the synthesized full-length peptide and via a 1,3-dipolar cycloaddition between an azide ($-N_3$) and an alkyne (Huisgen reaction). A disadvantage of this method is here the necessity of adding copper or copper-containing compounds to perform the 1,3-dipolar cycloaddition. Many peptides complex copper, particularly those comprising sulphur, i.e. comprising methionine and/or cysteine; arginine and lysine can also bind to copper. The copper is therefore difficult to remove and due to the toxicity of the remaining copper the method is not applicable in all cases, especially not for the purification of peptide therapeutics. Another disadvantage is that the solid phase used for purification is not intended or suitable for reuse.

It is therefore the object of the invention to provide a method for the purification of peptides that does not require a complete HPLC system and is also suitable for sulphur-containing or copper-binding peptides. In addition, it is the object of the invention to provide a method suitable for the purification of peptides that allows a regeneration and reuse of the solid phase used for purification. Furthermore, it is the object of the invention to provide a compound that allows binding between the N-terminal amino group of a full-length peptide and a solid phase.

In a first aspect of the present invention, this object is achieved by a compound of the general formula $$X_1\text{-}L\text{-}X_2 \qquad (1),$$

wherein
$X_1$ is selected from

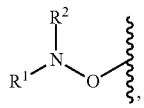
(2)

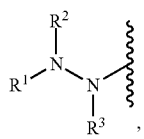
(3)

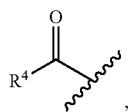
(4)

wherein each $R^1$ and $R^2$ is independently from each other selected from H or B, wherein at least $R^1$ or $R^2$ is B, wherein
$R^3$ is selected from H or B,
wherein B is an acid labile amine protecting group, wherein
$R^4$ is selected from H, $C_1$-$C_{12}$-alkyl or aryl, wherein the aldehyde or keto group may be protected by an acid labile protecting group,
L is selected from functional linkers, that are cleavable nucleophilically from $X_2$ under basic conditions, in particular L is of the form -T-U—, wherein
T is a spacer between $X_1$ and U, wherein in particular T is selected from substituted or unsubstituted —$C_1$-$C_{12}$-alkyl-, in particular $C_1$-$C_6$-alkyl, in particular $C_1$-$C_3$-alkyl, —$R^5$—C(=O)—NH—$R^6$—, —$R^5$—C(=O)—O—$R^6$—, —$R^5$—C(=O)—O—, —C(=O)—O—$R^6$—, —C(=O)—NH—$R^6$—, —C(=O), —C(=O)—O—, —$R^5$-phenyl-$R^6$—, —$R^5$-phenyl-, -phenyl-$R^6$—, -phenyl-,
wherein $R^5$ and $R^6$ are independently from each other selected substituted or unsubstituted $C_1$-$C_{12}$-alkyls, in particular $C_1$-$C_6$ alkyls, particularly $C_1$-$C_3$ alkyls, and wherein
U is the cleavage activating part of the functional linker, wherein the activating part is formed to stabilize an anion formed during an basic cleavage from $X_2$,
$X_2$ is of the form —Y—Z, wherein
Y is selected from —O—C(=O)— or —S(=O)$_2$—, and
Z is an electron-withdrawing leaving group.

In the context of the present invention, the term "cleavage activating part" of a molecule relates to a structural element of a reactive function.

"Reactive function" relates to a compound that can be excited (activated) to generate a reactive species. This can be a catalyst or a change in pH value, for example. The reactive species is able to form a covalent bond, for example a carbamate bond, in a short time with a suitable reaction partner. The reactive function thus comprises groups which, once activated, react specifically with other functional groups, for example amine or amide.

The term "spacer" relates to a moiety of several atoms within a molecule, which itself is free of reactive functions and spatially separates two functional groups of the molecule. The spacer is a covalently bonded chain or ring structure consisting of carbon, phosphorus, sulphur, silicon, nitrogen and/or oxygen atoms. The spacer may contain substituting groups which do not contribute to the distance between the functional groups to be separated.

The term "group" relates to a moiety of several atoms within a molecule. Typically, these atoms form functional units such as a spacer, a reactive function or a molecular structure that exerts a mesomeric or inductive effect.

The terms "functional linker" or "linker" relate to a functional group that connects two functional units within a molecule. The linker is covalently bound to the functional groups.

The terms "linker", "linker molecule", "linker system" and "capture compound" relate to a molecule that connects two other molecules by forming a covalent bond to each of the other molecule. The covalent bonds to the functional groups of the two other molecules only occur under certain reaction conditions. In particular, the terms "linker", "linker molecule", "linker system" and "capture compound" relate to compounds which fall under formula (1) and can generate a connection between an N-terminus of a peptide and a solid support.

The term "substituted" relates to the addition of an atom or a molecular group or compound to a parent compound. The substituent group or compound can be added protected or unprotected to one or more available positions in the parent molecule. The substituent group or compound itself may be substituted or unsubstituted and bound directly or through a linking group or moiety such as an alkyl, amide or hydrocarbonyl group to the parent molecule. Substituting groups or compounds include, for example, halogens, oxygen, nitrogen, sulfur, hydroxyl, alkyl, alkenyl, alkynyl, carboxyl (—C(O)OR$^a$), acyl (—C(O)R$^a$) groups, aliphatic, alicyclic groups, alkoxy, amino ((—N(R$^b$)(R$^c$)), imino (=NR$^b$), amido (—C(O)N(R$^b$)(R$^c$) or —N(R$^b$)C(O)R$^a$) groups, hydrazine derivatives (—C(NH)NR$^a$R$^b$), triazoles, tetrazoles (CN$_4$H$_2$), azido (—N$_3$), nitro (—NO$_2$), cyano (—CN), isocyano (—NC), cyanato (—OCN), isocyanato (—NCO), thiocyanato (—SCN); isothio-cyanato (—NCS); carbamido (—OC(O)N(R$^b$)(R$^c$) or —(R$^b$)C(O)OR$^a$) groups, thiols (—SR$^b$), sulfinyl (—S(O)R$^b$), sulfonyl (—S(O)$_2$R$^b$), sulfonamidyl (—S(O)$_2$N(R$^b$)(R$^c$) or —N(R$^b$)S(O)$_2$R$^b$) groups and fluorinierte fluorinated moieties such as —CF$_3$, —OCF$_3$, —SCF$_3$, —SOCF$_3$ or —SO$_2$CF$_3$. R$^a$, R$^b$ and R$^c$ is independently from each other H or a further substituting group.

The term "alkyl" relates to a saturated straight or branched hydrocarbon chain with up to 12 carbon atoms. Examples of preferred alkyl groups are methyl, ethyl, propyl, butyl, isopropyl, n-hexyl, octyl, decyl groups.

The term "aryl" relates to a hydrocarbon moiety with alternating double and single bonds between the carbon atoms, wherein a ring structure is formed.

The term "leaving group" relates to a functional group within a molecule that exerts a -M and/or -I effect and can thus easily be cleaved off, wherein the binding electron pair remains with the leaving group after cleavage.

The term "surface-modified solid support" relates to a solid structure such as sepharose, agarose or cellulose units, silica gel or polydextrans modified by synthetic or natural polymers such as polysaccharides, polylysine, polyarylamide, polyethylene glycol (PEG) or acrylamide-PEG copolymers. The surface of the solid support is characterized by aldehyde, ketone, hydroxylamine or hydrazine groups.

In some embodiments, Z is an electron-withdrawing leaving group which exerts a -M and/or -I effect and, in the case of a heterolytic bond cleavage, keeps the binding electron pair.

In some embodiments, Z is an electron-withdrawing leaving group, wherein the acid corresponding to the anion of the leaving group is characterized by a pks value of less than five.

In some embodiments, Z is an electron-withdrawing leaving group, wherein the acid corresponding to the anion of the leaving group is characterized by a pks value of less than five, and wherein the leaving group in particular exerts a -M and/or -I effect, and in the case of a heterolytic bond cleavage keeps the binding electron pair.

In some embodiments, U is the cleavage activating part of the functional linker, wherein the activating part is a group which allows anion formation by -M and -I effects, and stabilizes the resulting anionic compound by an electron pair shift, wherein this stabilization leads to a heterolytic bond cleavage between U and X$_2$.

In some embodiments, B is selected from Boc (—C=OOtBu), trityl (—C(Ph)$_3$), Mmt (—C(Ph)$_2$C$_6$H$_4$OMe), DMT (—C(Ph)(C$_6$H$_4$OMe)$_2$), Cbz (—C=OOCH$_2$Ph), benzylideneamine (=CPh), phtalimides (=(CO)$_2$C$_6$H$_4$), p-toluenesulfonamides (—SO$_2$C$_6$H$_4$Me), benzylamine (—CH$_2$Ph), acetamides (—COMe), trifluoroacetamide (—COCF$_3$), Dde (1-(4,4-dimethyl-2,6-dioxocyclohex-1-ylidene)-3-ethyl) and 1-(4,4-dimethyl-2,6-dioxocyclohex-1-ylidene)-3-methylbutyl (ivDde), wherein particularly B is Boc.

In some embodiments, the acetal- or ketal protecting groups are selected from

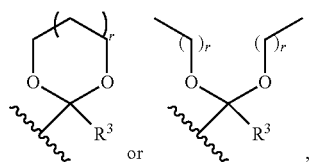

wherein r is 0 to 12, in particular 0, 1 or 2.

The skilled person is aware that the inventive compound can also be formed with other acid labile protecting groups.

In some embodiments, T is selected from substituted or unsubstituted C$_1$-C$_{12}$-alkyl, in particular C$_1$-C$_6$-alkyl, in particular C$_1$-C$_3$-alkyl, —R$^5$—C(=O)—NH—R$^6$—, —R$^5$—C(=O)—O—R$^6$—, —R$^5$—C(=O)—O—, —C(=O)—O—R$^6$—, —C(=O)—NH—R$^6$—, —C(=O)—, —C(=O)—O—, wherein R$^5$ and R$^6$ are independently from each other selected substituted or unsubstituted $C_1$-$C_{12}$-alkyls, in particular $C_1$-$C_6$-alkyls, in particular $C_1$-$C_3$-alkyls.

When T is a substituted alkyl, the substituents are particularly those that increase water solubility, for example —$SO_3H$, —$CO_2H$ or —$NO_2$.

In some embodiments, T is selected from —$CH_2$—, —$CH_2$—C(=O)—NH—$(CH_2)_2$—, —$(CH_2)$—C(=O)—O—$(CH_2)_2$—, —$CH_2$—C(=O)—O—, —C(=O)—O—, —C(=O)—O—$(CH_2)_2$—, and —C(=O)—.

In some embodiments, T is selected from —$CH_2$—, —$CH_2$—C(=O)—NH—$(CH_2)_2$—, —C(=O)—O—$(CH_2)_2$—, —$CH_2$—C(=O)—O—, and —C(=O)—.

In some embodiments, U of the moiety T-U—Y is selected from the moieties according to the formulas (5), (6), (7), (8), (9), (10) and (11), in particular from (5), (6), (8), (9) and (10),

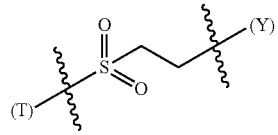

(5)

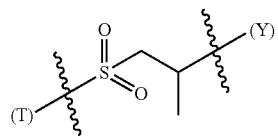

(6)

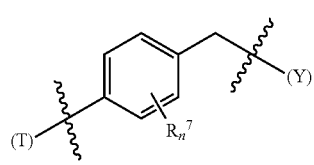

(7)

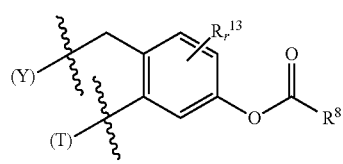

(8)

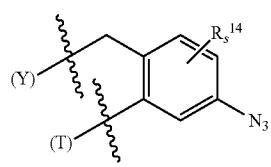

(9)

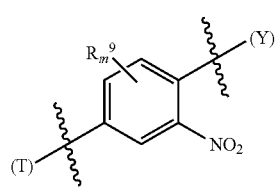

(10)

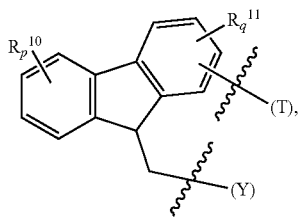

(11)

wherein $R^8$ is selected from $C_1$-$C_6$-alkyl, $CF_3$, $CH_2CF_3$,

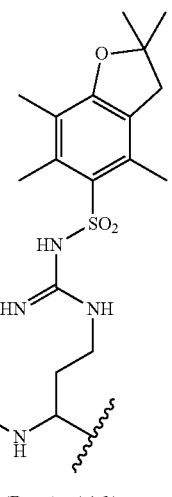

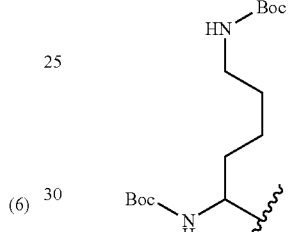

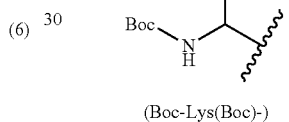 and 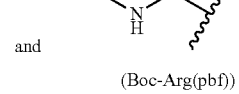, (Boc-Lys(Boc)-)   (Boc-Arg(pbf))

in particular from Boc-Lys(Boc)-,
wherein $R^7_n$, $R^9_m$, $R^{10}_p$, $R^{11}_q$, $R^{13}_r$ and $R^{14}_s$ is selected from $C_1$-$C_6$-alkyl or —I and/or -M-effects generating substituents, in particular $C_1$-$C_3$-alkyls, —F, —Cl, —Br, —I, —CN—$NO_2$, —$N_3$, —$CF_3$, —$SO_3H$, —$CO_2H$,
wherein n equals 0, 1, 2, 3 or 4, in particular n is 0 oder 1, in particular 0,
wherein m equals 0, 1, 2 or 3, in particular m is 0 oder 1, in particular 0,
wherein p equals 0, 1, 2, 3 or 4, in particular p is 0 oder 1, in particular 0,
wherein q equals 0, 1, 2 or 3, in particular q is 0 oder 1, in particular 0,
wherein r equals 0, 1, 2 or 3, in particular r is 0 oder 1, in particular 0,
wherein s equals 0, 1, 2 or 3, in particular s is 0 oder 1, in particular 0.

In some embodiments, $R^7_n$, $R^9_m$, $R^{10}_p$, $R^{11}_q$, $R^{13}_r$ and $R^{14}_s$ is selected from $C_1$-$C_6$-alkyl or —I and/or -M-effects generating substituents, in particular $C_1$-$C_3$-alkyls, —F, —Cl, —Br, —I, —CN—$NO_2$, —$N_3$, —$CF_3$, —$SO_3H$, and —$CO_2H$, in particular —F, —Cl, —Br, —I, —$NO_2$, and —$N_3$
wherein n equals 0, 1, 2, 3 or 4, in particular n is 0 oder 1, in particular 0,
wherein m equals 0, 1, 2 or 3, in particular m is 0 oder 1, in particular 0,
wherein p equals 0, 1, 2, 3 or 4, in particular p is 0 oder 1, in particular 0,
wherein q equals 0, 1, 2 or 3, in particular q is 0 oder 1, in particular 0, wherein r equals 0, 1, 2 or 3, in particular r is 0 oder 1, in particular 0, wherein s equals 0, 1, 2 or 3, in particular s is 0 oder 1, in particular 0.

In some embodiments, $R^7_n, R^9_m, R^{10}_p, R^{11}_q, R^{13}_r$ and $R^{14}_s$ is selected from substituents that increase water solubility, in particular from $-NO_2$, $-SO_3H$ and $-CO_2H$.

In some embodiments, Z is selected from the group $-F$, $-Cl$, $-Br$, $-I$, $-N_3$, $-SR^{12}$, $-OCF_3$, $-OCH_2CF_3$, $-OSO_2CF_3$, $-SO_2C_6H_4CH_3$, $-SO_2CF_3$, $-SO_2CH_3$

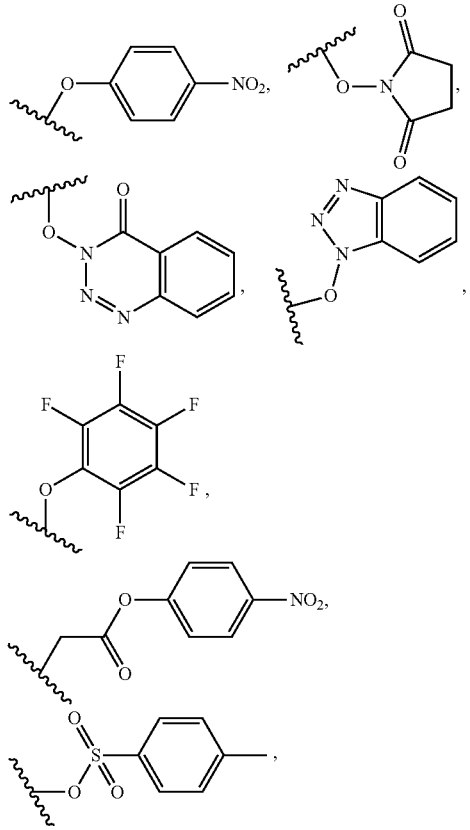

wherein $R^{12}$ is a $C_1$-$C_6$-alkyl-, an aryl- or a benzyl residue.

In some embodiments, Z is selected from $-Cl$,

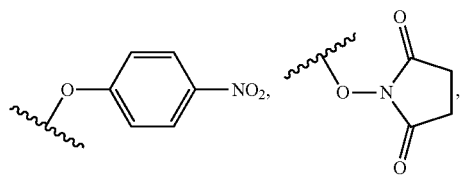 [SMILES: *Oc1ccc([N+](=O)[O-])cc1 ; *ON1C(=O)CCC1=O]

in particular from and

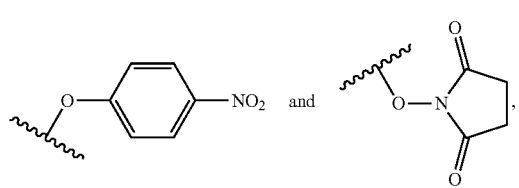 [SMILES: *Oc1ccc([N+](=O)[O-])cc1 ; *ON1C(=O)CCC1=O]

In some embodiments, $X_1$ is a moiety of formula (2) or (3), wherein $R^3$ is H, $R^1$ and $R^2$ comprise a Boc protecting group or $R^1$ is H and $R^2$ is a Boc protecting group.

In some embodiments, $X_1$ is a moiety of formula (3), wherein $R^1$ and $R^3$ is H and $R^2$ is a Boc protecting group.

In some embodiments, Y is of the form $-O-C(=O)-$.

In some embodiments, T is of the form $-CH_2-C(=O)-NH-(CH_2)_2-$, $-CH_2-C(=O)-O-(CH_2)_2-$, $-C(=O)-O-(CH_2)_2-$ and U is a moiety of formula (5) or (6),

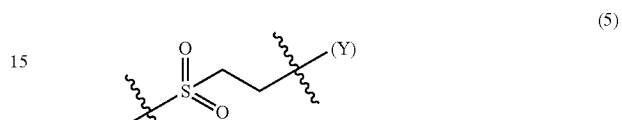

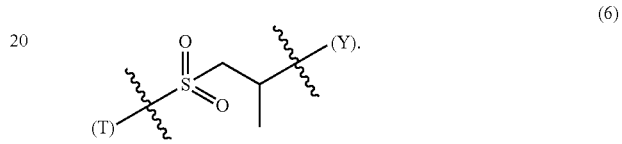

In some embodiments, T is of the form $-C(=O)-O-(CH_2)_2-$ or $-CH_2-C(=O)-NH-(CH_2)_2-$ and U is a moiety of formula (6).

In some embodiments, T is of the form $-C(=O)-O-(CH_2)_2-$ or $-CH_2-C(=O)-NH-(CH_2)_2-$ and U is a moiety of formula (6).

In some embodiments, T is of the form $-CH_2-C(=O)-NH-(CH_2)_2-$ and U is a moiety of formula (6).

In some embodiments, T is of the form $-CH_2-C(=O)-O-$ or $-C(=O)-O-$ and U is a moiety of formula (7),

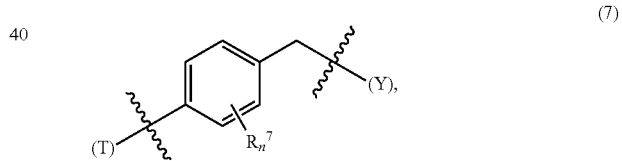

wherein $R^7$ is selected from $C_1$-$C_6$-Alkyl or $-I$ and/or -M-effect generating substituents, in particular $C_1$-$C_3$-alkyl, $-F$, $-Cl$, $-Br$, $-I$, $-CN$, $-NO_2$, $-N_3$, $-CF_3$, $-SO_3H$, and $-CO_2H$, wherein n equals 0, 1, 2, 3 or 4, in particular 0 or 1, in particular 0.

In some embodiments, T is of the form $-CH_2-C(=O)-O-$, and U is a moiety of formula (7), wherein n equals 0.

In some embodiments, T is of the form $-CH_2-$, and U is a moiety of formula (8),

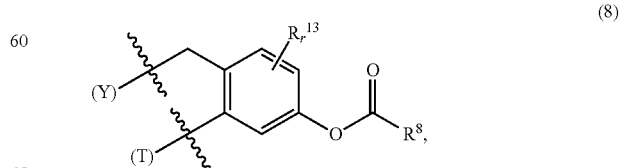

wherein $R^8$ is Boc-Lys(Boc)- and r equals 0.

In some embodiments, T is of the form —CH₂— or —(C═O)—, and U is a moiety of formula (9),

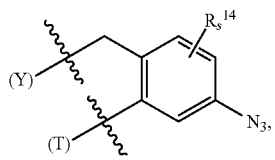

(9)

wherein s equals 0.

In some embodiments, T is of the form —CH₂—, and U is a moiety of formula (9).

In some embodiments, T is of the form —C(═O)—, and U is a moiety of formula (10),

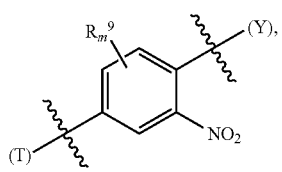

(10)

wherein m equals 0, Y is of the form —SO₂— and Z is Cl.

In some embodiments, the compound of formula (1) is selected from 2,2-dimethylpropanoyloxy-[2-[2-[2-(4-nitrophenoxy)carbonyloxypropylsulfonyl]ethylamino]-2-oxo-ethoxy]amino] 2,2-dimethylpropanoate (formula (14)), [[2-[2-[2-(4-nitrophenoxy) carbonyloxypropylsulfonyl]ethylamino]-2-oxoethoxy]amino] 2,2-dimethylpropanoate (formula (15)), [2-(4-chlorosulfonyl-3-nitrobenzoyl)hydrazino] 2,2-dimethylpropanoate (formula (16)), [2,2-dimethylpropanoyloxy-[2-[4-[(2,5-dioxopyrrolidine-1-yl)oxycarbonyloxymethyl]phenoxy]-2-oxo-ethoxy]amino] 2,2-dimethylpropanoate (formula (17)), [2-(2,2-dimethylpropanoyloxy)-2-[2-[2-[2-(2,5-dioxopyrrolidine-1-yl)oxycarbonyloxypropylsulfonyl]ethylamino]-2-oxo-ethyl]hydrazino] 2,2-dimethylpropanoate (formula (18)), [2-(2,2-dimethylpropanoyloxy)-2-[2-[2-[2-(2,5-dioxopyrrolidine-1-yl)oxycarbonyloxyethylsulfonyl]ethylamino]-2-oxo-ethyl]hydrazino] 2,2-dimethylpropanoate (formula (19)), [2-[5-azido-2-[(2,5-dioxopyrrolidine-1-yl)oxycarbonyloxymethyl]benzoyl]hydrazino]2,2-dimethylpropanoate (formula (20)), [3-[(2,2-dimethylpropanoyloxyamino)carbamoyl]-4-[(2,5-dioxopyrrolidine-1-yl)oxycarbonyloxymethyl]phenyl] 2,6-bis(2,2-dimethylpropanoyloxyamino) hexanoate (formula (21)), [2-[2-[2-[2-(4-nitrophenoxy)carbonyloxypropylsulfonyl]ethylamino]-2-oxo-ethyl]hydrazino] 2,2-dimethylpropanoate (formula (22)), [2-[2-[2-[2-(2,5-dioxopyrrolidine-1-yl) oxycarbonyloxy-propylsulfonyl]ethylamino]-2-oxo-ethyl]hydrazino] 2,2-dimethylpropanoate (formula (23)), [2-[2-[4-[(2,5-dioxopyrrolidine-1-yl)oxycarbonyloxymethyl]phenoxy]-2-oxo-ethyl]hydrazino]2,2-dimethyl-propanoate (formula (24)), [2-[2-[2-(4-nitrophenoxy)carbonyloxyethylsulfonyl]ethoxycarbonyl] hydrazino] 2,2-dimethylpropanoate (formula (25)), [3-[[2-(2,2-dimethylpropanoyloxy)hydrazino]methyl]-4-[(2,5-dioxopyrrolidine-1-yl) oxycarbonyloxymethyl]phenyl] 2,6-bis(2,2-dimethylpropanoyloxyamino)hexanoate (formula (26)), [2-[[5-azido-2-[(2,5-dioxopyrrolidine-1-yl) oxycarbonyloxymethyl]phenyl]methyl]hydrazino] 2,2-dimethylpropanoate (formula (27)),

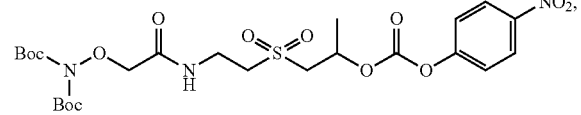

(14)

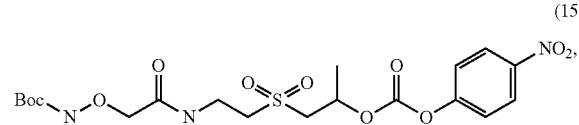

(15)

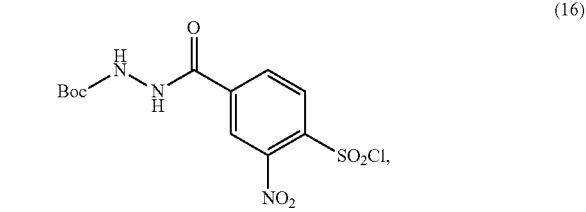

(16)

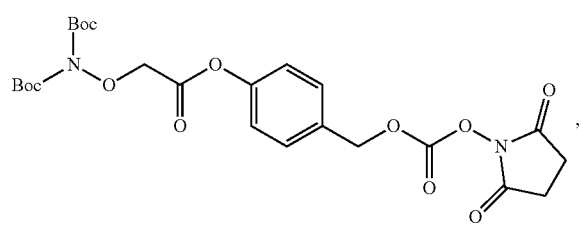

(17)

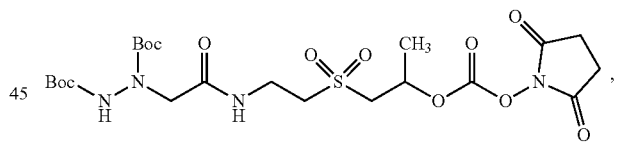

(18)

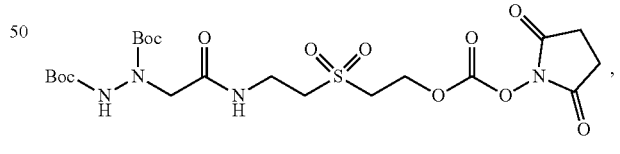

(19)

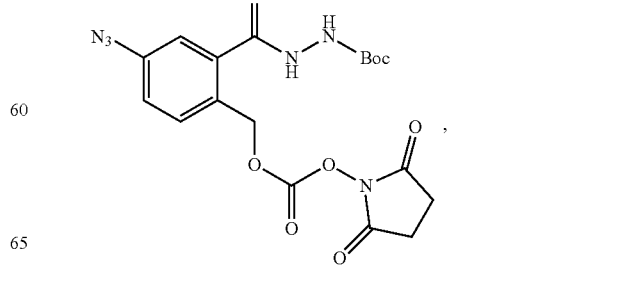

(20)

-continued

(21)
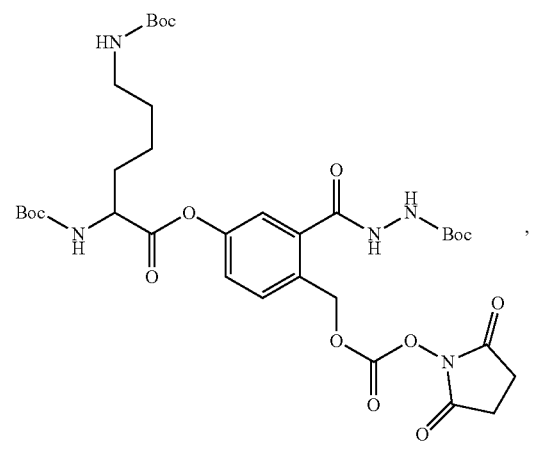

(22)
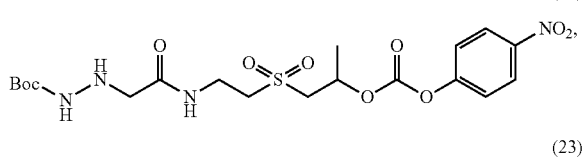

(23)
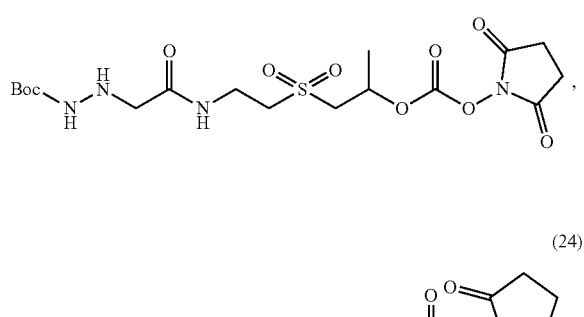

(24)

(25)
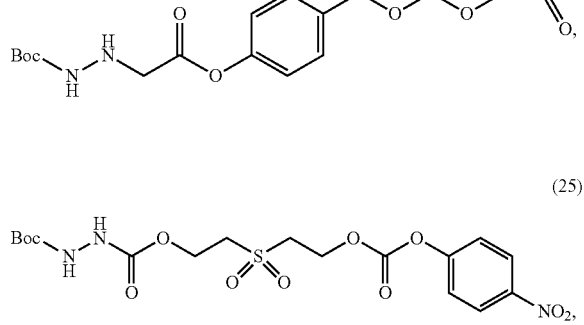

(26)
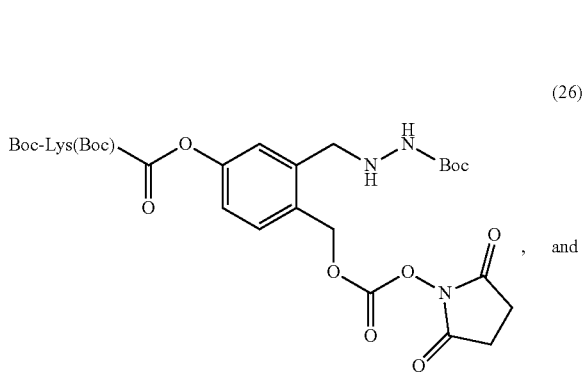

, and

-continued

(27)
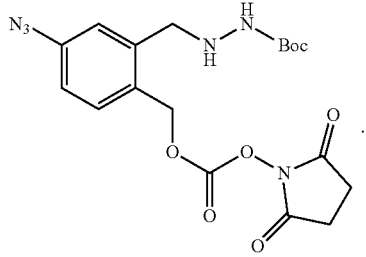

In some embodiments, the compound of formula (1) is selected from a compound of formula (14), (15), (16), (17), (18), (19), (20) and (21).

In some embodiments, the compound of formula (1) is selected from a compound of formula (16), (19), (20) and (21).

In a further aspect, the object of the invention is achieved by the use of a compound according to the first aspect that forms a connection between the N-terminal amino group of a full-length peptide and a solid phase.

In a further aspect, the object of the invention is achieved by a compound of formula (12), $X_1$-L-Y-PEP (12), wherein $X_1$, L and Y are defined according to the first aspect and its embodiments, and wherein PEP comprises a full-length peptide that is bound to $X_2'$ via its N-terminus.

In a further aspect, the object of the invention is achieved by a compound of formula (13), D-$X_1'$-L-Y-PEP (13), wherein D is a surface-modified solid support, which is characterized in that the surface is modified by synthetic or natural polymers, wherein $X_1'$ is of the form —NH—O—, —NH—NH— or —C(=O)— and wherein L, Y and PEP are defined according to the first aspect and its embodiments.

In some embodiments, the surface-modified solid support D is characterized by modified polysaccharides.

In some embodiments, the surface-modified solid support D is characterized by aldehyde- or hydrazine-modified sepharose/agarose or cellulose.

In a further aspect, the object of the invention is achieved by a method for the purification of peptides, in particular of peptides prepared by solid phase peptide synthesis (SPPS), comprising the following steps:

i. contacting a composition of a full-length peptide to be purified and at least one impurity, in particular at least one acetylated truncated sequence, with a capture compound that is defined according to the first aspect and its embodiments, and subsequent reaction to a compound of formula (12), ii. cleavage of the acid labile protecting groups by addition of an acid, iii. contacting the composition of ii. with a surface-modified solid support, wherein a covalent hydrazone or oxime bond is formed between the capture compound and the solid support, and a compound of formula (13) is provided, iv. cleavage of the full-length peptide from the solid support.

In some embodiments, step i. comprises contacting a mixture of full-length peptide and truncated sequences, that are still at the solid phase (the synthesis resin), with a compound (capture molecule) of the general formula $X_1$-L-$X_2$ wherein $X_1$, $X_2$ and L are as defined above and wherein the step of contacting leads to a reaction of the compound $X_1$-L-$X_2$ at $X_2$ with the free N-terminal amino group of the full-length peptide to form a covalent bond. Cleavage of the peptides from the solid phase (synthesis resin) is performed by means of acids, whereby a mixture of full-length peptide covalently bound to the capture molecule and acetylated truncated sequences of peptides from a solid phase peptide synthesis (SPPS) is obtained. Separation of the solid and liquid phase is performed for example by filtration. The non-peptide impurities are removed by precipitation in ether at a temperature of −78° C. to 0° C.

Preferably, the acid mixture is added to the provided ether, wherein all peptide material precipitates and organic impurities remain in the ether. The etheric solution is then separated from the peptide mixture, e.g. by centrifugation. The peptide mixture is obtained as an amorphous solid.

In some embodiments, step ii. comprises dissolution of the amorphous solid from step i) in an at least partially aqueous buffer solution at a pH value between 2 and 4, preferably between 2.5 and 3.5, particularly preferably at 3. The pH is adjusted by adding suitable acids or bases.

In some embodiments, step iii. comprises contacting the mixture from ii) with a surface-modified solid support (purification resin) to covalently bind the full-length peptides, that are modified with the capture molecule (step i), by forming a hydrazone or oxime bond. The addition of amines and/or acetic acid as a catalyst to improve the kinetics of the binding reaction is particularly advantageous here.

The truncated peptide sequences not bound to the solid support via the hydrazone/oxime bond are removed by washing with organic solvents and/or with water and aqueous buffer solution, preferably with the addition of chaotropic substances, in order to dissolve peptides which may not be covalently bound.

In some embodiments, step iv. comprises separating the full-length peptides from the solid phase by cleaving the linker L from Y under basic (nucleophilic) conditions, wherein Y is released in the form of $CO_2$ or $SO_2$.

Upon cleavage of the full-length peptide starting from the formula (13) (D-X1'-L-Y-PEP), the full-length peptide (PEP), $CO_2$ or $SO_2$ (Y') and D-X1'-L or D' and $X_1$'-L' are formed.

In some embodiments, the solid support comprises on its surface the functional groups aldehyde, ketone, hydroxylamine and hydrazine.

In some embodiments, the solid support comprises on its surface the functional group —O—$CH_2$—CHO.

In some embodiments, the solid support comprises on its surface the functional groups —$ONH_2$ or —$N_2H_3$.

In some embodiments, the solid phase is separated from the desired full-length peptides by filtration; the solid phase (purification resin, D) is regenerated by treatment with hydrazine ($H_4N_2$) and/or ammonium hydroxide $H_4NOH$ and/or aldehydes and/or ketones and/or washing with water.

For cleaving the peptides form the synthesis resin (step i), acids are used, organic and inorganic acids with a pks value below 4 are preferred here. Acids selected from the group of acids containing fluorine are particularly suitable: trifluoroacetic acid (TFA), hydrofluoric acid (HF) and triflourmethanesulfonic acid. Hydrobromic acid (HBr), hydrochloric acid (HCl), sulphurous acid ($H_2SO_3$), sulphuric acid ($H_2SO_4$), phosphoric acid ($H_3PO_4$), nitric acid ($HNO_3$) or methanesulfonic acid are also suitable.

For the precipitation in step i) organic solvents are used which are in liquid state at the precipitation temperatures; such solvents are generally known to the skilled person. Organic solvents from the group of ethers are preferred, particularly diethyl ethers and/or methyl tert-butyl ethers are preferred. Alkanes which are in liquid state at the precipitation temperatures can also be used, wherein n-hexane and n-pentane are particularly preferred. Suitable, at least partially aqueous buffer solutions which are used in step ii) are known to the skilled person, namely buffers which have a buffer capacity in the pH range 2-5, thus buffers with the anions: citrate, malate, format, lactate, succinate, acetate, pivalate, and phosphate in combination with the cations: sodium, potassium, ammonium ($NH_4$, $NMe_4$, $NEt_4$, $NPr_4$, $NBu_4$, $HNC_5H_5$).

Organic or inorganic acids, preferably HCl and as bases preferably alkali metal and/or alkaline earth metal hydroxides, particularly preferably NaOH and/or KOH, can be used for adjusting the pH value.

For better solubility of the peptide it may be advantageous in step ii) to add water-miscible organic solvents to the system, such solvents are generally known to the skilled person and may be selected from the group: dimethylformamide (DMF), acetonitrile, tetrahydrofuran (THF), dioxane, pyridine, acetone, dimethyl sulfoxide (DMSO), methanol, ethanol, 1-propanol, 2-propanol, 1-butanol, formamide, N-methylpyrolidone (NMP).

Amines and/or acetic acid may be added to the aqueous solution to accelerate immobilization in step iii). Amines may be selected from the group consisting of: pyridine, piperidine, methylamine, ethylamine, propylamine, butylamine, aniline and dimethylamine.

Synthetic and natural polymers can be used as surface-modified solid support (purification resin) in step iii). The surface modification is such that it reacts with $X_1$ to hydrazones or oximes. If $X_1$ is a moiety according to formula (2) or (3), the surface modification consists of aldehyde or ketone groups, which then react accordingly to hydrazones or oximes. If $X_1$ is an aldehyde or ketone function of the general formula (4), the surface modification should comprise —$ONH_2$, or —$N_2H_3$. Surface-modified natural as well as biopolymers are preferred as solid supports, particularly preferably surface-modified polysaccharides. Most preferred is the use of aldehyde-modified sepharose/agarose and cellulose, wherein $X_1$ is a moiety of formula (3), wherein $R^1$ and $R^3$ are H.

In step iii (washing of the full-length peptides bound to the purification resin) can be washed with water, aqueous washing solutions or organic solvents. Suitable chaotropic substances to the aqueous washing solution in step iii. are: barium salts, guadinium hydrochloride, guadinium thiocyanates, thiocyanates, perchlorates, iodides, butanol, phenol, thiourea, urea, or ammonium sulfate. Solvents may be selected from the group of: dichloromethane (DCM), trichloromethane, carbon tetrachloride, ethyl acetate, diethyl ether, methyl tert-butyl ether, acetic acid, 2,2,2-trifluoroethanol, hexafluoroisopropanol, dimethylformamide (DMF), acetonitrile. Tetrahydrofuran (THF), dioxane, pyridine, acetone, dimethyl sulfoxide (DMSO), methanol, ethanol, 1-propanol, 2-propanol, 1-butanol, phenol, formamide and N-methylpyrolidone (NMP).

The cleavage in step iv. is performed by bases in aqueous solutions or organic solvents which dissolve peptides. Bases may be selected from the group of: LiOH, NaOH, KOH, ammonium ($NH_4$, $NMe_4$, $NEt_4$, $NPr_4$, $NBu_4$, $HNEt(iPr)_2$, $HNMe_3$, $HNEt_3$, $HNPr_3$, $HNBu_3$, $HNC_5H_5$) hydroxides, piperidine, methylamine, ethylamine, propylamine, butylamine, hydrazine, hydroxylamine, methylhydrazine and O-methylhydroxylamine. Organic solvents which dissolve peptides may be selected from the group of: dimethylformamide (DMF), acetonitrile. Tetrahydrofuran (THF), dioxane, pyridine, acetone, dimethyl sulfoxide (DMSO), methanol, ethanol, 1-propanol, 2-propanol and 1-butanol.

Filtration in step iv) is preferably performed using commercially available syringe reactors or filter systems. The filter pore sizes should be between 10 and 100 μm.

In some embodiments, after or during cleavage of the full-length peptide from the solid support, the solid support D is cleaved from the residue $X_1$-L of the capture compound and the solid support is regenerated.

A particular advantage of the method according to the invention is the reversibility of the hydrazone and oxime bond.

The method described herein can be used like affinity chromatography due to the equilibrium nature of the hydrazone/oxime bond. After washing out or away the impurities and cleaving the base-labile linker and thus obtaining the target peptide, the purification resin can be regenerated again and is thus accessible for further purification. If there are originally aldehyde or keto groups on the surface of the purification resin, washing with acidic aqueous solution in which aldehydes or ketones are dissolved restores the aldehyde or ketone function. If there are originally hydrazine or hydroxylamine derivatives on the surface of the purification resin, washing with acidic aqueous solution with hydrazine or hydroxylamine restores the hydrazine or hydroxylamine function. The same material is used as for protein purification by affinity chromatography, sepharose/agarose.

Furthermore, the method can be applied on cellulose, which is the most common biomaterial on earth and therefore available at low cost.

Proteins are normally purified by affinity chromatography, and this method is also very cost-effective, efficient and scalable compared to HPLC purification. Due to the low pressures and higher loading densities, affinity chromatography is also much better suited for large synthesis quantities than HPLC.

In a subaspect of the first aspect of the present invention, the object is achieved by a compound which establishes as a linker a connection between the N-terminal amino group of a full-length peptide and a solid phase. The compound according to the invention is of the general formula $X_1$-L-$X_2$, wherein
$X_1$ is selected from

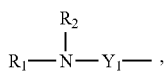

wherein $Y_1$=O, N and wherein $R_1$ and $R_2$ may be the same or different and $R_1$ and $R_2$ is H or B, wherein B is a non-base-labile protecting group for an amino group which provides amines under acidic conditions.

In a preferred embodiment, B is selected from the group: Boc (—C=OOtBu), trityl (—C(Ph)$_3$), Mmt (—C(Ph)$_2$C$_6$H$_4$OMe), DMT (—C(Ph)(C$_6$H$_4$OMe)$_2$), Cbz (—C=OOCH$_2$Ph), benzylidenamine (=CPh), phthalimide (=(CO)$_2$C$_6$H$_4$), p-toluenesulfonamide (—SO$_2$C$_6$H$_4$Me), benzylamine (—CH$_2$Ph), acetamide (—COMe), trifluoroacetamide (—COCF$_3$), Dde (1-(4,4-dimethyl-2,6-dioxocyclohex-1-ylidene)-3-ethyl) and 1-(4,4-dimethyl-2,6-dioxocyclohex-lylidene)-3-methylbutyl (ivDde).

The skilled person is also familiar with protecting groups from P. G. M. Wuts, T. W. Greene, Greene's Protective Groups in Organic Synthesis, 4th ed., Wiley, 2007, pages 696-926.

$X_1$ may alternatively be

wherein $R_3$=H, or $R_3$ is a saturated or unsaturated, branched or unbranched, substituted or unsubstituted aliphatic or aromatic chain having a length of up to 12 carbon atoms, and wherein the aldehyde or keto group may be protected in a manner known to the skilled person

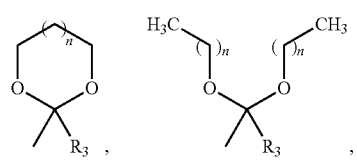

wherein n may be between 0 and 12, particularly preferably 0, 1 or 2.

All acetal-ketal protecting groups that can be cleaved under acidic conditions can serve as protected aldehyde or ketone. An overview can be found in particular in: P. G. M. Wuts, T. W. Greene, Greene's Protective Groups in Organic Synthesis, 4th ed., Wiley, 2007, page 435-477.

$X_2$ may be

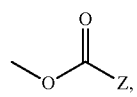

wherein Z is an electron-withdrawing protecting group which keeps the binding electron pair in the case of a heterolytic bond cleavage. In a particular embodiment, Z is selected from the group F, Cl, Br, J, N$_3$, SR$_8$ (wherein R$_8$ is defined as $R_3$), OCF$_3$, OCH$_2$CF$_3$,

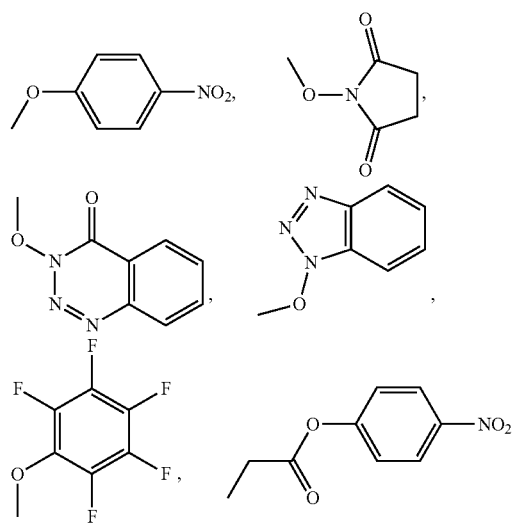

$X_2$ thus represents a carbamate precursor which is to form a carbamate with the amino group of the full-length peptide.

L is a functional linker that separates $X_1$ and $X_2$ and is cleavable under basic conditions (nucleophilic).

A selection of nucleophilically cleavable linkers can be found in F. Guillier, D. Drain, M. Bradley, Linkers and Cleavage Strategies in Solid-Phase Organic Synthesis and Combinatorial Chemistry, Chem. Rev. 2000, 100, 2091-2157.

In some embodiments, the compounds of the general formula $X_1$-L-$X_2$ are pharmaceutically acceptable salts thereof.

In some embodiments, the compound of the general formula $X_1$-L-$X_2$ is used as a linker which forms a connection between the N-terminal amino group of a full-length peptide and a solid phase.

In a preferred embodiment, the linker L is selected from the general structures a, b or c

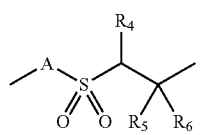

a

A: $C_0$-$C_2$, aromatic, aliphatic, unsaturated, saturated
$R_4$: H, alkyl or electron-withdrawing group
$R_5$, $R_8$: identical or different H or alkyl $C_1$-$C_{12}$

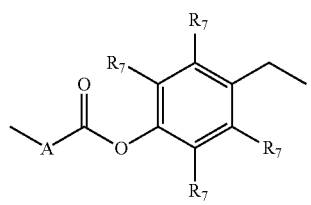

b $R_7$: identical or different H, electron-withdrawing group, or alkyl $C_1$-$C_{12}$

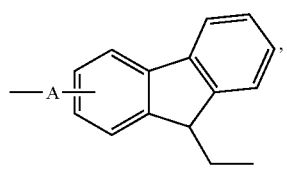

c wherein A is a saturated or unsaturated, branched or unbranched, substituted or unsubstituted aliphatic or aromatic chain having a length of 0 to 12 carbon atoms and wherein $R_4$=H, an alkyl chain of 0 to 12 carbon atoms or a group capable of attracting electrons by an inductive or mesomeric effect.

Wherein $R_5$ and $R_6$ may be the same or different and $R_5$, $R_6$=H, an alkyl chain having a length of 1 to 12 carbon atoms or a group capable of attracting electrons by an inductive or mesomeric effect. $R_7$ is H, an alkyl chain having a length of 1 to 12 carbon atoms or a group capable of attracting electrons by an inductive or mesomeric effect.

$R_8$ is as $R_3$.

In another aspect, the object of the invention is achieved by a method that comprises the following steps.

i) Contacting a mixture of full length peptide and truncated sequences, that are still at the solid phase (the synthesis resin), with a compound (capture molecule) of the general formula $X_1$-L-$X_2$ wherein $X_1$, $X_2$ and L are as defined above and wherein the step of contacting leads to a reaction of the compound $X_1$-L-$X_2$ at $X_2$ with the free N-terminal amino group of the full-length peptide to form a covalent bond.

ii) Cleavage of the peptides from the solid phase (synthesis resin) by means of acids and obtaining a mixture of full-length peptide covalently bound to the capture molecule and acetylated truncated sequences of peptides from a solid phase peptide synthesis (SPPS);

iii) Separation of the solid and liquid phase, e.g. by filtration;

iv) Removal of non-peptide impurities by precipitation in ether at a temperature of −78° C. to 0° C.

Preferably the acid mixture is added to the provided ether, wherein all peptide material precipitates and organic impurities remain in the ether. The etheric solution is then separated from the peptide mixture, e.g. by centrifugation. The peptide mixture is obtained as an amorphous solid;

v) Dissolution of the amorphous solid from step iv) in an at least partially aqueous buffer solution at a pH between 2 and 4, preferably between 2.5 and 3.5, particularly preferably of 3. The pH is adjusted by adding suitable acids or bases;

vi) Contacting the mixture from v) with a surface-modified solid support (purification resin) to covalently bind the full-length peptides modified with the capture molecule (step i) by forming a hydrazone or oxime bond. The addition of amines and/or acetic acid as a catalyst to improve the kinetics of the binding reaction is particularly advantageous here;

vii) Removal of truncated peptide sequences not bound to the solid support via the hydrazone/oxime bond by washing with organic solvents and/or with water and aqueous buffer solution, preferably with the addition of chaotropic substances, in order to dissolve peptides which may not be covalently bound; viii) Separation of the full-length peptides from the solid phase by cleaving the linker L under basic (nucleophilic) conditions;

ix) Filtration to separate the solid phase from the desired full-length peptides; and x) Regeneration of the solid phase (purification resin) by treatment with hydrazine ($H_4N_2$) and/or ammonium hydroxide $H_4NOH$ and/or aldehydes and/or ketones and/or washing with water.

For cleaving the peptides form the synthesis resin (step ii), acids are used, organic and inorganic acids with a pks value below 4 are preferred here. Acids selected from the group of acids containing fluorine are particularly suitable: trifluoroacetic acid (TFA), hydrofluoric acid (HF) and triflourmethanesulfonic acid. Hydrobromic acid (HBr), hydrochloric acid (HCl), sulphurous acid ($H_2SO_3$), sulphuric acid ($H_2SO_4$), phosphoric acid ($H_3PO_4$), nitric acid ($HNO_3$) or methanesulfonic acid are also suitable.

For the precipitation in step iii) organic solvents are used which are in liquid state at the precipitation temperatures; such solvents are generally known to the skilled person. Organic solvents from the group of ethers are preferred, particularly diethyl ethers and/or methyl tert-butyl ethers are preferred. Alkanes which are in liquid state at the precipitation temperatures can also be used, n-hexane and or n-pentane are particularly preferred.

Suitable, at least partially aqueous buffer solutions which are used in step v) are known to the skilled person, namely buffers which have a buffer capacity in the pH range 2-5, thus buffers with the anions: citrate, malate, format, lactate, succinate, acetate, pivalate, and phosphate in combination with the cations: sodium, potassium, ammonium ($NH_4$, $NMe_4$, $NEt_4$, $NPr_4$, $NBu_4$, $HNC_5H_5$).

Organic or inorganic acids, preferably HCl and as bases preferably alkali metal and/or alkaline earth metal hydroxides, particularly preferably NaOH and/or KOH, can be used for adjusting the pH value.

For better solubility of the peptide it may be advantageous in step v) to add water-miscible organic solvents to the system, such solvents are generally known to the skilled person and may be selected from the group: dimethylformamide (DMF), acetonitrile, tetrahydrofuran (THF), dioxane, pyridine, acetone, dimethyl sulfoxide (DMSO), methanol, ethanol, 1-propanol, 2-propanol, 1-butanol, formamide, N-methylpyrolidone (NMP).

Amines and/or acetic acid may be added to the aqueous solution to accelerate immobilization in step vi). Amines may be selected from the group consisting of: pyridine, piperidine, methylamine, ethylamine, propylamine, butylamine, aniline and dimethylamine.

Synthetic and natural polymers can be used as surface-modified solid support (purification resin) in step vi). The surface modification is such that it reacts with $X_1$ to hydrazones or oximes. If $X_1=$

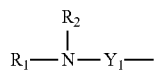

($Y_1=$NH, O) the surface modification consists of aldehyde or ketone groups, which then react accordingly to hydrazones or oximes. If $X_1$ is an aldehyde or ketone function of the general formula —$R_3C$=O, the surface modification should comprise a $NH_2$—$Y_1$—$R_7$ group ($R_7$=solid support). Surface-modified natural as well as biopolymers are preferred as solid supports, particularly preferably surface-modified polysaccharides. Most preferred is the use of aldehyde-modified sepharose/agarose and cellulose and $X_1=NH_2$—NH—C=OO—.

In step vi (washing of the full-length peptides bound to the purification resin) can be washed with water, aqueous washing solutions or organic solvents. Suitable chaotropic substances to the aqueous washing solution in step iii. are: barium salts, guadinium hydrochloride, guadinium thiocyanates, thiocyanates, perchlorates, iodides, butanol, phenol, thiourea, urea, ammonium sulfate. Solvents may be selected from the group: dichloromethane (DCM), trichloromethane, carbon tetrachloride, ethyl acetate, diethyl ether, methyl tert-butyl ether, acetic acid, 2,2,2-trifluoroethanol, hexafluoroisopropanol, dimethylformamide (DMF), acetonitrile. Tetrahydrofuran (THF), dioxane, pyridine, acetone, dimethyl sulfoxide (DMSO), methanol, ethanol, 1-propanol, 2-propanol, 1-butanol, phenol, formamide and N-methylpyrolidone (NMP).

The cleavage in step vii. is performed by bases in aqueous solutions or organic solvents which dissolve peptides. Bases may be selected from the group: LiOH, NaOH, KOH, ammonium ($NH_4$, $NMe_4$, $NEt_4$, $NPr_4$, $NBu_4$, $HNEt(iPr)_2$, $HNMe_3$, $HNEt_3$, $HNPr_3$, $HNBu_3$, $HNC_5H_5$) hydroxides, piperidine, methylamine, ethylamine, propylamine, butylamine, hydrazine, hydroxylamine, methylhydrazine and O-methylhydroxylamine. Organic solvents which dissolve peptides may be selected from the group: dimethylformamide (DMF), acetonitrile. Tetrahydrofuran (THF), dioxane, pyridine, acetone, dimethyl sulfoxide (DMSO), methanol, ethanol, 1-propanol, 2-propanol and 1-butanol. The filtration in step viii) is preferably performed using commercially available syringe reactors or filter systems. The filter pore sizes should be between 10 and 100 μm.

In some embodiments, the method according to the invention is characterized in that the solid and liquid phases are separated by filtration.

In some embodiments, the method according to the invention is characterized in that in step vi. amines and/or acetic acid are added as catalyst.

In some embodiments, the method according to the invention is characterized in that the buffer solution in step v. has a pH value between 2.5 and 3.5 and preferably of 3.

In some embodiments, the method according to the invention is characterized in that the removal in step vii. is performed by washing with organic solvents and/or with water and aqueous buffer solution, preferably with the addition of chaotropic substances, in order to dissolve peptides which may not be covalently bound.

In some embodiments, the method according to the invention is characterized in that the separation of the full-length peptides from the solid phase in step viii. is performed by cleaving the linker L under basic (nucleophilic) conditions.

In some embodiments, the method according to the invention is characterized in that for the separation of the peptides from the synthesis resin in step ii. acids with a pks value below 4 are used.

In some embodiments, the method according to the invention is characterized in that for precipitation in step iii. organic solvents from the group of ethers, particularly preferably diethyl ethers and/or methyl tert-butyl ethers or n-hexane and or n-pentane are used.

In some embodiments, the method according to the invention is characterized in that synthetic and natural polymers are used as surface-modified solid support (purification resin), e.g. surface-modified polysaccharides, particularly preferably aldehyde-modified sepharose/agarose, or cellulose and $X_1=NH_2$—NH—C=OO—.

A particular advantage of the method according to the invention is the reversibility of the hydrazone and oxime bond.

The method described herein can be used like affinity chromatography due to the equilibrium nature of the hydrazone/oxime bond. After washing out or away the impurities and cleaving the base-labile linker and thus obtaining the target peptide, the purification resin can be regenerated again and is thus accessible for further purification. If there are originally aldehyde or keto groups on the surface of the purification resin, washing with acidic aqueous solution in which aldehydes or ketones are dissolved restores the aldehyde or ketone function. If there are originally hydrazine or hydroxylamine derivatives on the surface of the purification resin, washing with acidic aqueous solution with hydrazine or hydroxylamine restores the hydrazine or hydroxylamine function. The same material is used as for protein purification by affinity chromatography, sepharose/agarose.

Furthermore, the method can be applied on cellulose, which is the most common biomaterial on earth and therefore available at low cost.

Proteins are normally purified by affinity chromatography, and this method is also very cost-effective, efficient and scalable compared to HPLC purification. Due to the low pressures and higher loading densities, affinity chromatography is also much better suited for large synthesis quantities than HPLC.

In the following, without limiting the generality of the teaching, the invention will be explained by means of some examples with reference to the figures.

General Synthesis Scheme

The capture molecules according to the invention can be prepared according to the general synthesis scheme (1).

According to this scheme, the nucleophilic left part of the linker molecule can be varied between hydroxylamine and hydrazine. The cleavable part of the linker L can also be varied. A distinction can be made between sulfonlinkers and phenol ester linker systems. In addition, the right carbonate part of the linker system may have different leaving groups. This results in a plethora of possible combinations. The building blocks L1 and L3 are commercially available. L2 can be prepared according to scheme 2.

L1, L2:

Scheme 2: Synthesis of the linker building blocks L1 and L2.

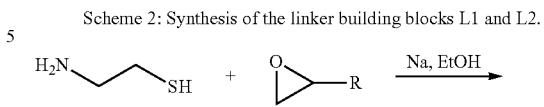

Scheme 1: General synthesis scheme for linker synthesis according to a modular principle. a) i) $CH_2Cl_2$, ii) L1 and L2 are oxidized to sulfones with mCPBA in $CH_2Cl_2$ for the thioether building blocks. DCC: dicyclohexylcarbodiimide, DIEA: diisopropylethylamine, Boc: tert-butyloxycarboxyl.

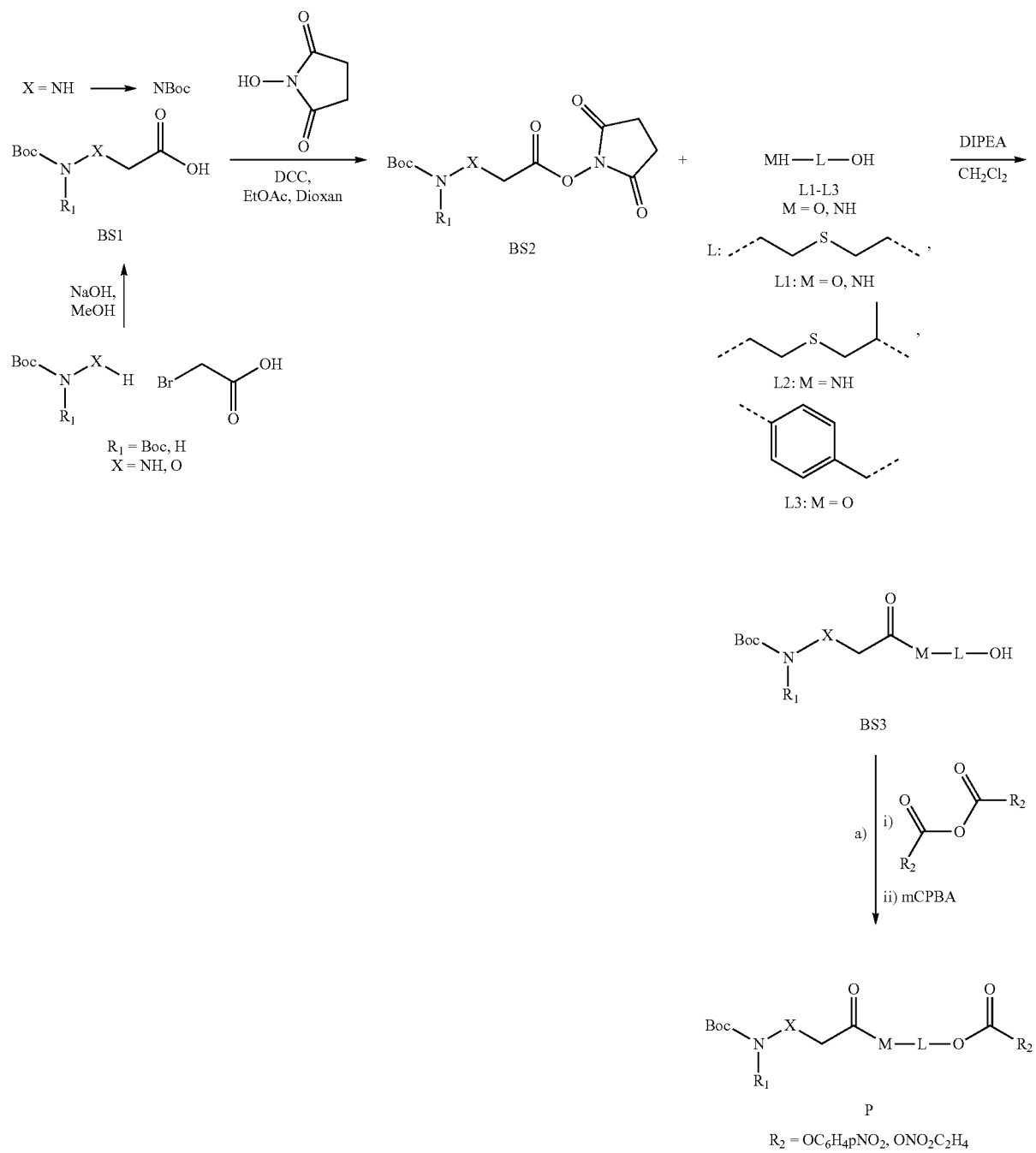

-continued

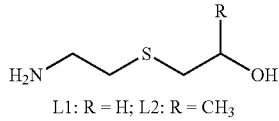

L1: R = H; L2: R = CH₃

DESCRIPTION OF THE FIGURES

FIG. 5 shows an alternative representation to FIG. 1.

SEQ ID Nos: 1 to 10 show peptides from examples 1, 2 and 4.

EXAMPLES

Example 1. Demonstration of the Reversibility of the Hydrazone/Oxime Bond

The reversible binding of the peptide to aldehyde-modified agarose beads is demonstrated in the following using the example of hydrazone binding; due to the electronic similarity (see also A. Dirksen, P. Dawson, Bioconjugate Chem. 2008, 19, 2543-2548.), the results are applicable to the oxime bond. It is shown that the equilibrium can be controlled by the addition of hydrazine ($N_2H_4$).

Figure 1:
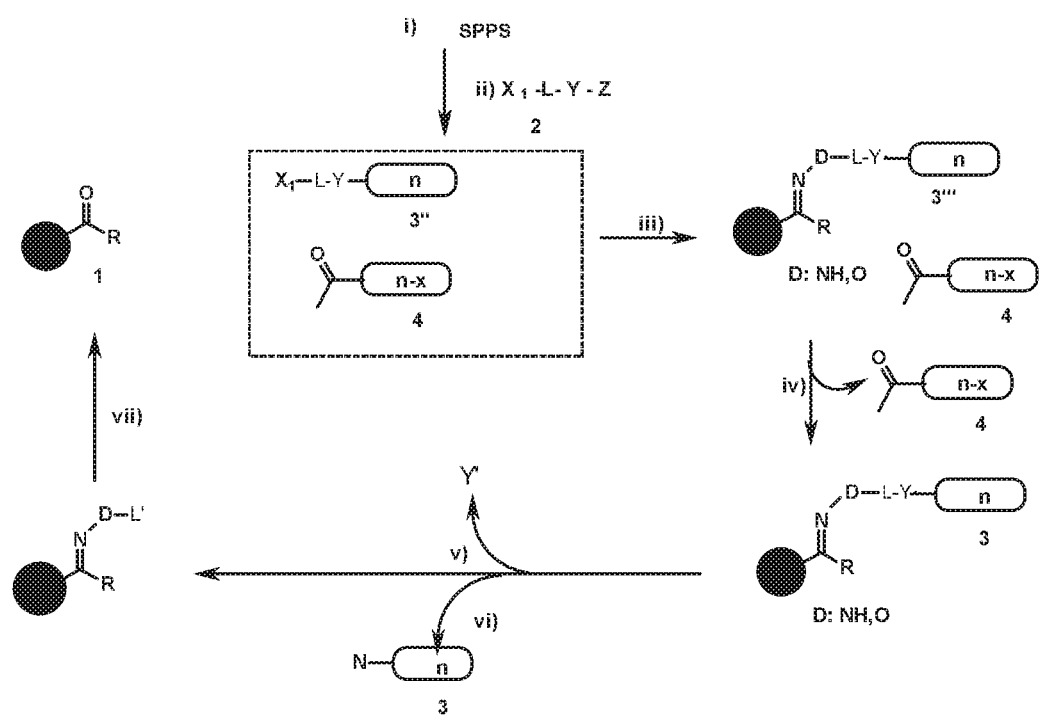
FIG. 1 shows a schematic representation of the method according to the invention to illustrate the same. i) SPPS with acetylation after each coupling, n-fold repetition; ii) addition of molecule X1-L-X2, iii) immobilization; iv) washing; v) basic cleavage; vi) filtration; vii) regeneration. 1: purification resin, 2: capture molecule, 3: native peptide (desired product), 4: truncated sequences, x=1 to n, n: full-length peptide, n-x: truncated sequences.
Figure 2:
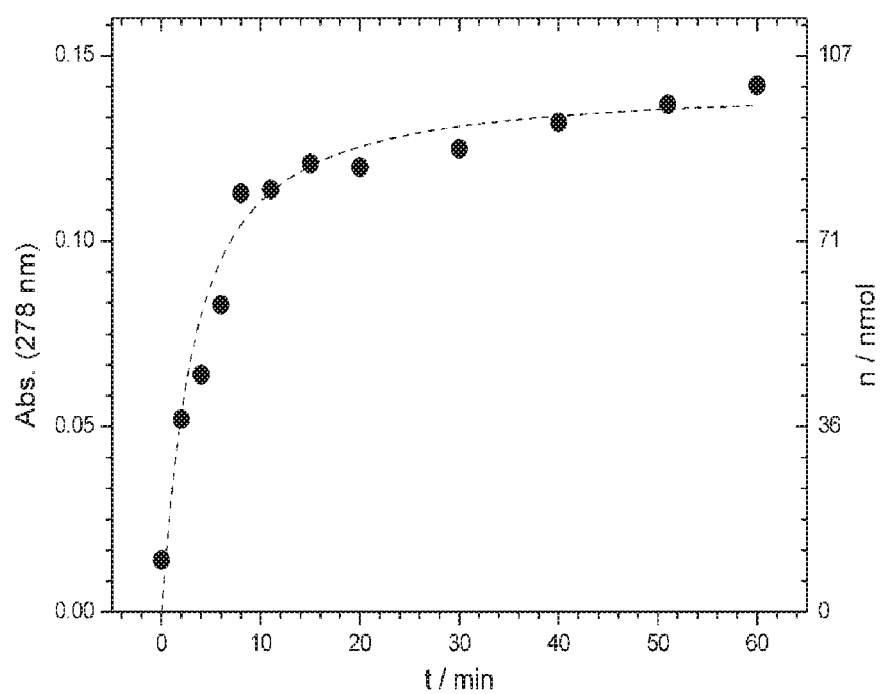
FIG. 2 shows the absorption at 278 nm when measuring the supernatant after cleaving off the peptide (compound 3 in FIG. 6) with 0.5 vol. % $N_2H_4$ to demonstrate the reversibility of the hydrazone bond from example 1. Abs.: Absorption of the supernatant of peptide-loaded aldehyde-modified agarose support at 278 nm. t: Time elapsed after the addition of a 0.5% hydrazine solution in minutes (min). n: Amount of peptide in the supernatant in nmol calculated on the basis of absorption. Dashed line: Non-linear regression according to Hill with the formula: $y=0.142*x/(3.16+x)$, $R^2=92$, $t_{1/2}=3.16$ min.
Figure 6:
FIG. 6 shows Scheme 3: Reversibility of the hydrazone bond between a peptide and a purification resin. i) 0.1 M $NH_4OAc$, pH=4, 0.1 M $PhNH_2$, 30 min; ii) 0.5% $N_2H_4$, 5 mM TCEP; the peptide sequence (white characters in black area) is assigned to SEQ ID NO: 1.

Peptide 3 was bound to the support 1 in the conjugation buffer (0.1 M $NH_4OAc$, 0.1 M $PhNH_2$, pH=3) in 30 min (FIG. 6: Scheme 3). Subsequently, it was washed with water and the supernatant removed. Then a solution of 0.5 volume percent hydrazine hydrate was added to the beads and the absorption was measured at 278 nm of the supernatant (200 L) at a time interval (with the ND-I000 spectrophotometer from NanoDrop Technologie). It was found that after 10 min, 80% of the peptide can be measured in the supernatant. After another 50 minutes, 86% of the peptide was recovered. A half-life of three minutes was determined by non-linear regression, FIG. 2 shows the adsorption at 278 nm when measuring the supernatant after addition of $N_2H_4$.

Example 2: Purification of a Peptide after Native Chemical Ligation (NCL)

The purification of a peptide from a complex system containing a mixture of peptide material as well as organic and inorganic impurities was performed.

Figure 3:
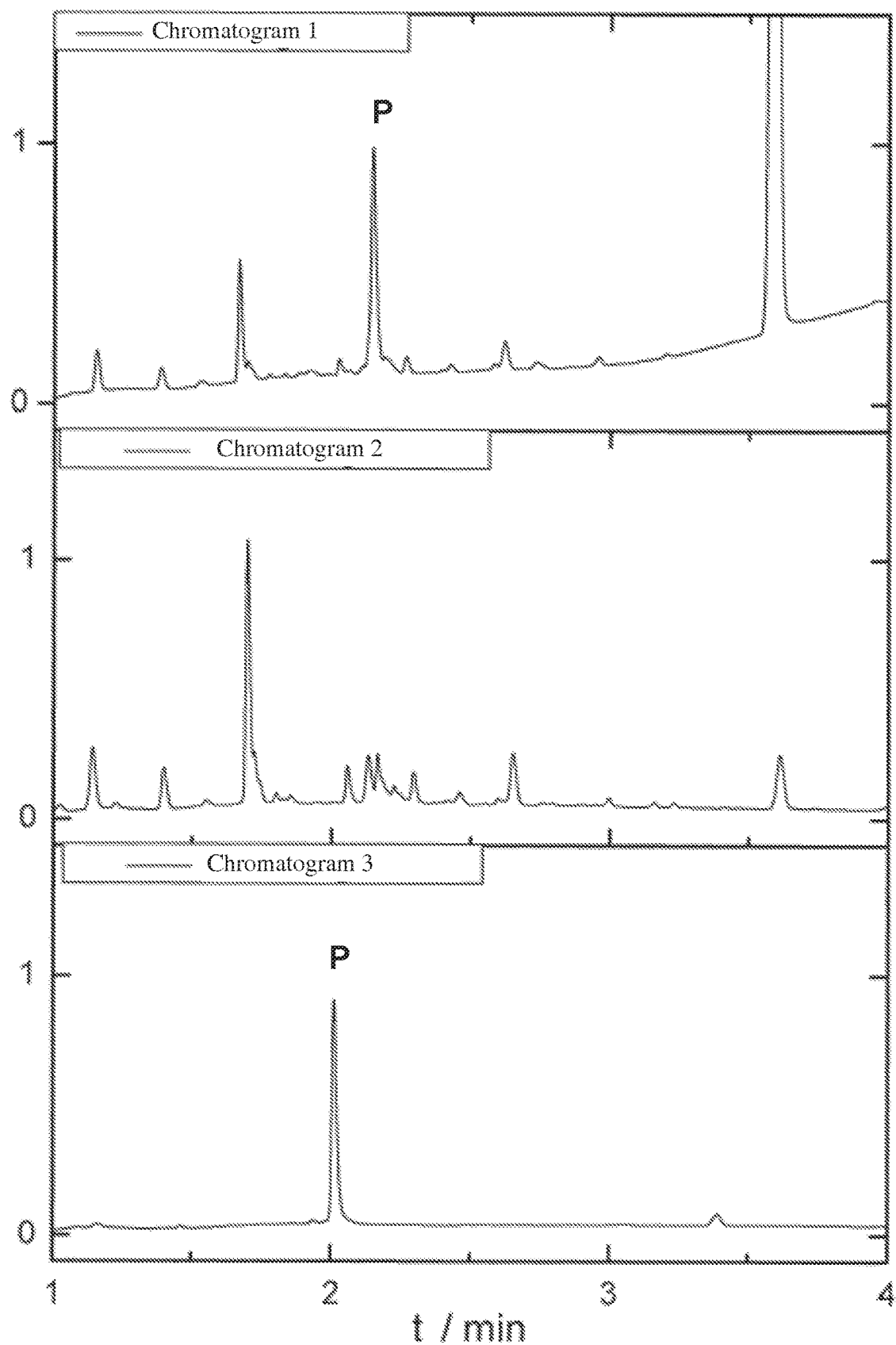
FIG. 3 shows chromatograms of the individual phases upon purification according to the invention of a peptide after Native Chemical Ligation (NCL) from Example 2. Chromatogram 1 shows the desired product (P) in the reaction mixture of the NCL after 24 hours. Chromatogram 2 shows the supernatant after 30 minutes of immobilization. Chromatogram 3 shows the desired product (P) after 30 minutes of washing and cleavage. P: Peak of the desired product.
Figure 7:
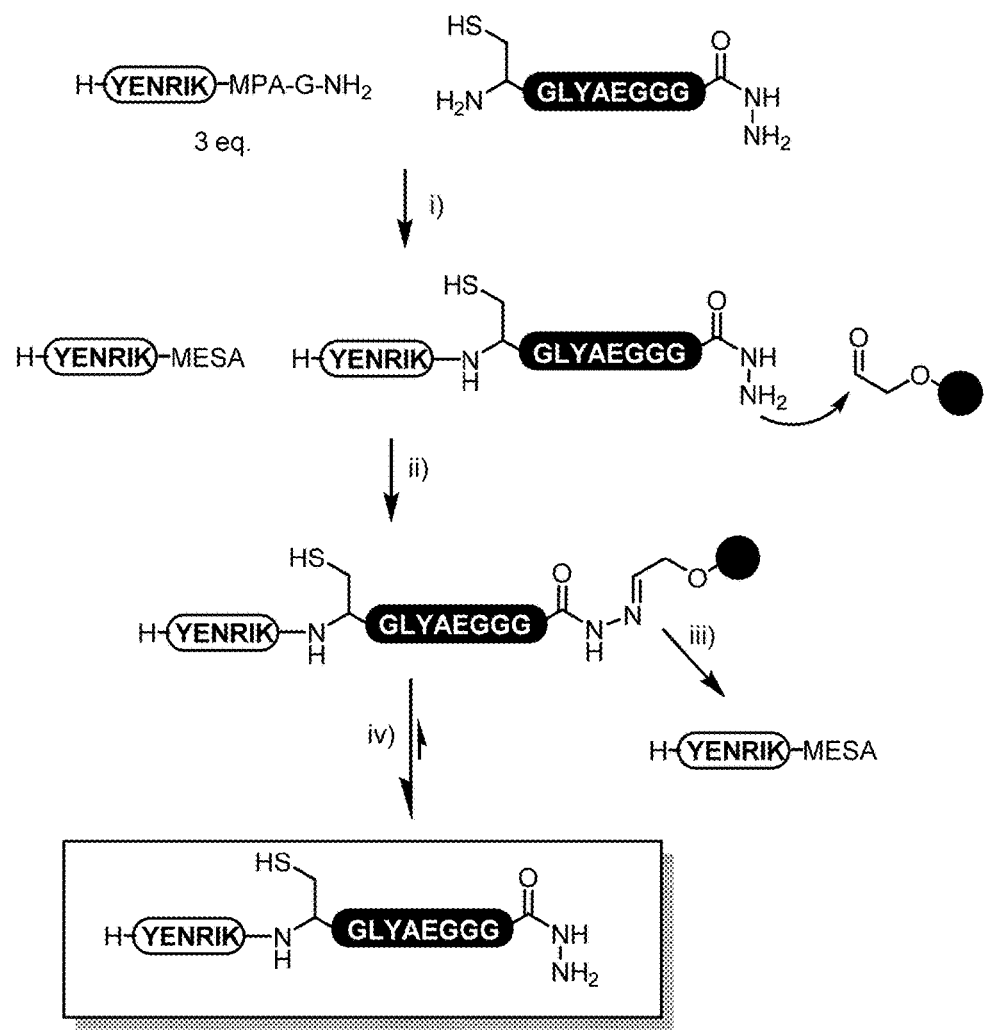
FIG. 7 shows Scheme 4: Purification of a peptide after native chemical ligation i) 0.1 M $Na_2HPO_4$, 3 M Gdn*HCl, 20 mM TCEP, 50 mM MesNa, 1% (v/v) PhSH, pH=7, 15 h; ii) Addition sepharose resin and 2-fold vol. of 0.1 M $NH_4OAc$ pH=2.5, pH=4, 30 min; iii) Washing $H_2O$, EtOH; iv) $N_2H_4$, 4 mM TCEP, 30 min. The peptide sequences are assigned to SEQ ID NO: 1 (white characters in black area) and SEQ ID NO: 2 ("YENDRIK" in white area).

The mixture to be purified was obtained after an NCL (FIG. 7: scheme 4). This reaction is performed in an aqueous buffer system and is used to synthesize larger peptides and protein domains. After 24 h reaction time of the NCL the raw mixture is obtained, which essentially contained the desired ligation product and the thioester (H-YENRIK-MESA), which was used in excess. This can be seen in the chromatogram (UPLC-MS from Waters, Acquity H-Class PDA/QDa, on Polaris C18 A 5 μm 250/4 column) in FIG. 3.

Twice the volume of conjugation buffer was added to the ligation buffer (0.1 M $Na_2HPO_4$, 20 mM TCEP, 50 mM MesNa, pH=7). Modified sepharose beads were subsequently added and the two-phase system was shaken for 30 minutes. The supernatant of the sepharose gel was analysed using UPLC-MS (FIG. 3, chromatogram 2); no mass that could be assigned to the ligation product could be found in the connected mass spectrometer. However, since an absorption signal can be observed at the retention time of the product, it also becomes apparent that impurities can be removed that could not be separated by means of HPLC. After washing with water and some ethanol and acetonitrile, 0.5 vol. % hydrazine hydrate in water was added to the peptide-loaded sepharose beads and the supernatant was analysed after 30 minutes, wherein the chromatogram 3 (FIG. 3) was obtained. This shows a high peptide purity (desired product) of over 90%.

Figure 8:
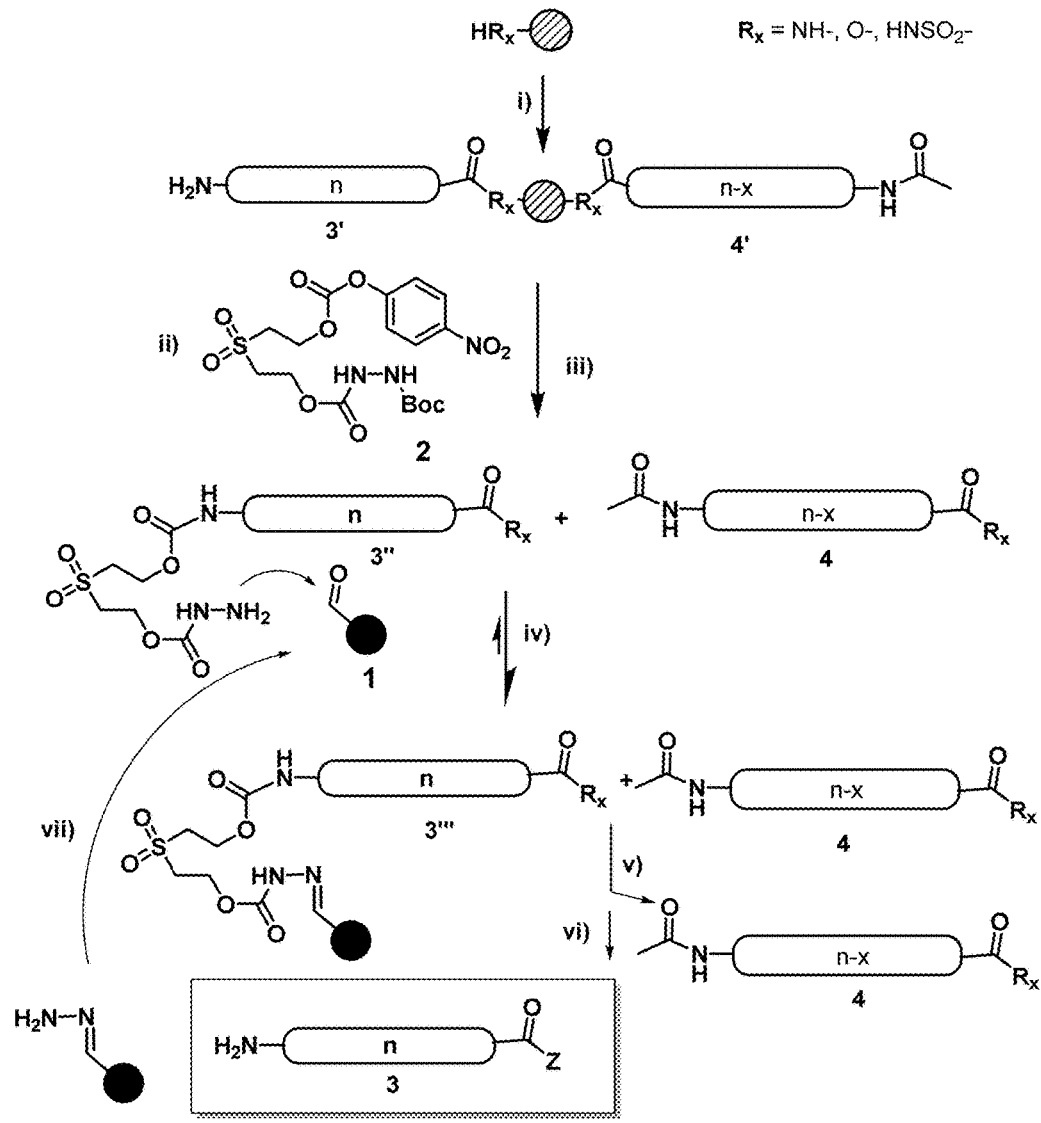
FIG. 8 shows Scheme 5: Purification according to the invention of a peptide mixture after solid phase peptide synthesis (SPPS) i) SPPS with acetylation after each coupling, n-fold repetition; ii) Addition of molecule 2; iii) Cleavage with TFA; iv) Immobilization on purification resin by addition of $Ph-NH_2$ at pH 3-4; v) Washing with water and buffer; vi) Base 5% $NH_4OH$; vii) Regeneration of the purification resin 1 by addition of $H_2O$/acetone/TFA (49,5/49,5/1). 1: purification resin, 2: capture molecule, 3: native peptide (desired product), 4: truncated sequences, x=1 to n, n: full-length peptide, n-x: truncated sequences.

Example 3: Exemplary Purification of a Peptide Mixture after Solid Phase Peptide Synthesis The reaction scheme (scheme 5) of purification according to the invention is shown in FIG. 8.

Figure 9:
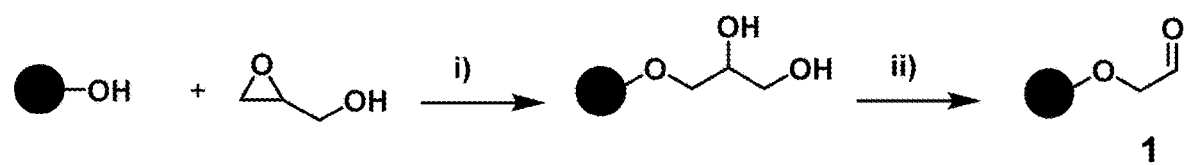
FIG. 9 shows Scheme 6: Functionalization of agarose beads i) NaOH, $NaBH_4$, $H_2O$, r.t, o/n, 18 h; ii) 20 mM $NaIO_4$, $H_2O$, r.t, 1 h.

After solid phase synthesis (SPPS), a capture molecule 2 (FIG. 8) is added to the last coupled amino acid. An important prerequisite for this is that acetylation was complete in the previous steps. Afterwards, all truncated sequences and the capture-molecule-modified full-length peptide are cleaved from the resin. Subsequently, non-peptide impurities are removed by ether precipitation and the crude peptide mixture is dissolved in an acetate buffer which has a pH value of 3-4 and to which 0.1 M aniline is added as catalyst. This solution is now added to functionalized sepharose beads 1 (FIGS. 8 and 9). This material is applied in protein purification as a material for affinity chromatography. Sepharose has the advantage of being easily penetratable by the peptides. The sepharose is previously aldehyde modified (see FIG. 9), the aldehyde modification of the sepharose is known from: J. Guisan, Enzyme Microb. Technol. 1988, 10, p. 375.

Hereby, only peptides that carry the capture molecule with the hydrazide function are anchored to the solid support. Amines, which theoretically can also react with aldehydes, are protonated at the pH value to be used and therefore not nucleophilic enough for an attack on aldehyde. The truncated sequences that are still in the sepharose can be washed out with water. Treatment of sepharose with a basic solution, e.g. ammonia in water, causes the capture molecule to decompose and the full-length peptide dissolves. The solution can then be lyophilized, wherein ammonia is removed. Subsequently, the peptide is obtained in pure form as a solid. One advantage of the method is its rapid immobilization and broad applicability to different peptides.

Example 4: Exemplary Regeneration of the Purification Resin

After peptide purification with capture molecule 2 (FIG. 8), the original aldehyde function of 1 remains blocked with hydrazine, in order to make the purification resin available again for a new purification cycle, the resin needs to be regenerated and thus the aldehyde function needs to be restored. This is achieved by shifting the equilibrium by adding aldehydes or ketones. The exemplary feasibility was shown as follows. The purification resin 1 was divided into three equal aliquots (I, II, III) and two aliquots (II, III) were treated with hydrazine in conjugation buffer for 30 min. Subsequently, it was washed with water and Aliquot III was washed seven times with a mixture of water, acetone and TFA (49.5:49.5:1). Then all aliquots were treated with FmocN$_2$H$_3$ in conjugation buffer for 14 h and then each washed five times with water, DMF and water. This was followed by two treatments with DMF/Piperidine (20%) for 4 min each and then the UV absorption of the resulting fluoren piperidine adduct was measured at 301 nm in the supernatant (SmartSpec™Plus Spectrophotometer from BioRad in 1 mL semi-micro quartz cuvettes from Hellma). The untreated aliquot I showed a load of 27 µmol/g; the aliquot II without regeneration a load of 18 µmol/g (67% of I), and the regenerated resin showed a load density of 25 µmol/g (93% of I). This experiment shows the successful regeneration of the purification resin.

TABLE 1

UV-absorption and loading density of purification resins after different regeneration treatments

| Aliquot | A (301 nm) | S (µmol/g) | Proportion [%] |
|---|---|---|---|
| I | 0.286 | 27 | 100 |
| II | 0.199 | 18 | 67 |
| III | 0.267 | 25 | 93 |

Example 5: Purification of a Peptide Mixture

The method according to the invention for the purification of peptides was applied to seven peptides of different polarity, which were H-TLADEVSASLAK-OH (SEQ ID NO: 3) (7) fragment 427-438 of the tau protein relevant to Alzheimer's disease, H-ATLADEVSASLAK-NH$_2$ (SEQ ID NO: 4) (8) fragment 427-439 of tau, the cysteinyl peptide H-CQWSLHRKRHLARTLLTAAREPRPAPPSSNKV-NH$_2$ (SEQ ID NO: 5) (8) from protein progona-doliberin-2 (9), H-GIGKFLHSAKKFGKAFVGEIMNS-NH$_2$ (SEQ ID NO: 6) Magainin (10), H-YLFFYRKSV-NH$_2$ Terts72Y (SEQ ID NO: 7) (11), H-FPRPGGGGNGDFEEIPEEYL-NH$_2$ (SEQ ID NO: 8) Bivalirudin (12) and H-GRKKRRQRRRPQ-NH$_2$ TAT (SEQ ID NO: 9) (13).

The crude peptide mixture was dissolved in the conjugation buffer and added to the sepharose beads 1 within 30-60 min, subsequent washing with water and neutral aqueous solutions (4M urea, 1M table salt) all acetylated truncated sequences and other impurities could be removed. The cleavage of linker 2 (FIG. 10: scheme 7) was performed with 5% ammonia solution in water for 20 minutes, it was then neutralized in-situ with acetic acid and the solubility was increased.

Figure 4:
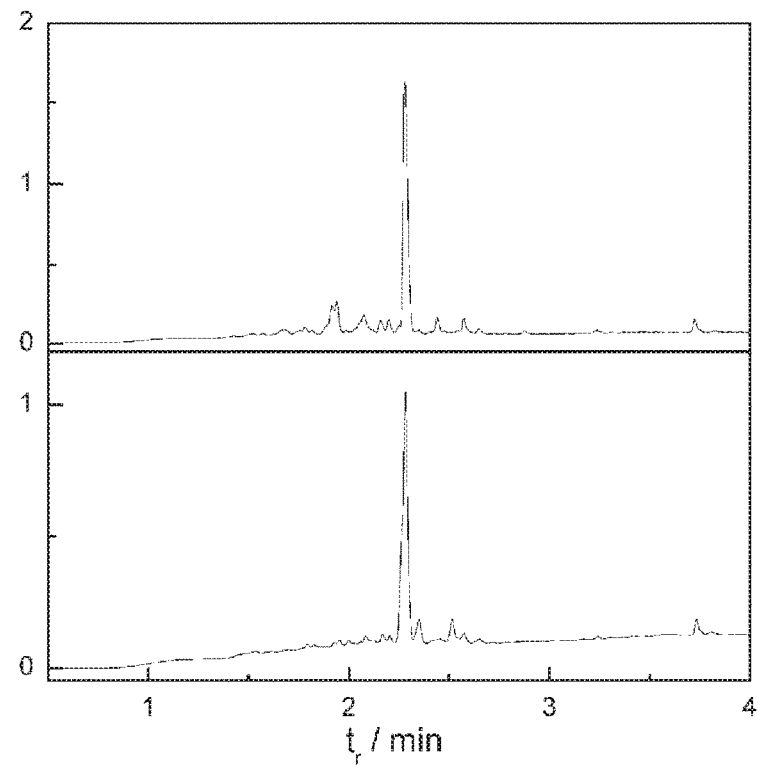
FIG. 4 shows chromatograms upon purification according to the invention of peptides 7-13 after solid phase peptide synthesis from example 4. The chromatograms, which are labeled with supernatant, show the impurities which could be separated by the method. FM=capture molecule according to invention; (a) peptide 7 (Tau1); (b) peptide 8 (Tau2); (c) peptide 9 (GNRH), (d) peptide 10 (Magainin); (e) peptide 11 (Terts72Y); (f) peptide 12 (bivalrudine); (g) peptide 13 (TAT), (h) peptide 14 (research peptide). Each upper diagram shows the peptide after synthesis and each lower diagram shows the peptide after purification.
Figure 4:
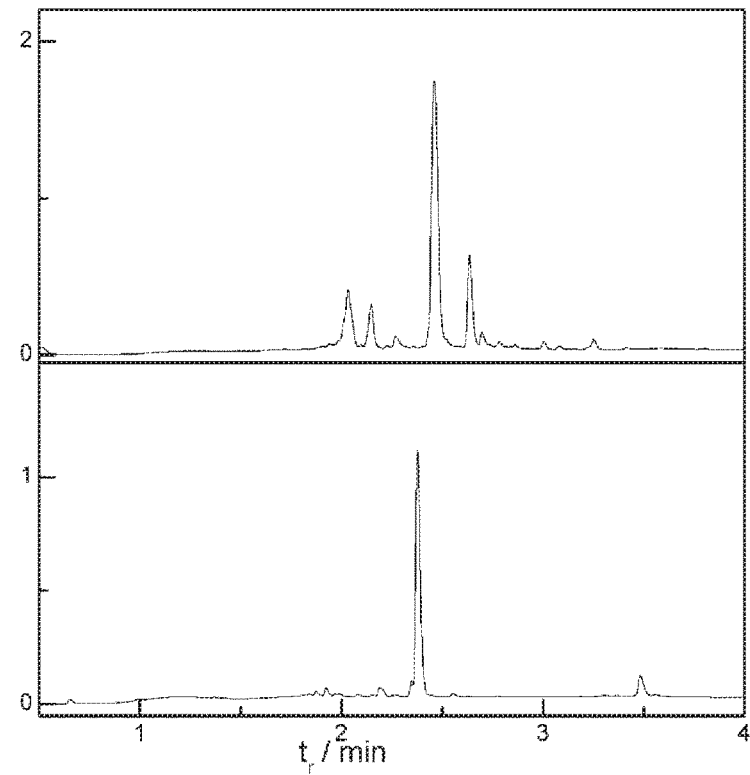
Figure 4:
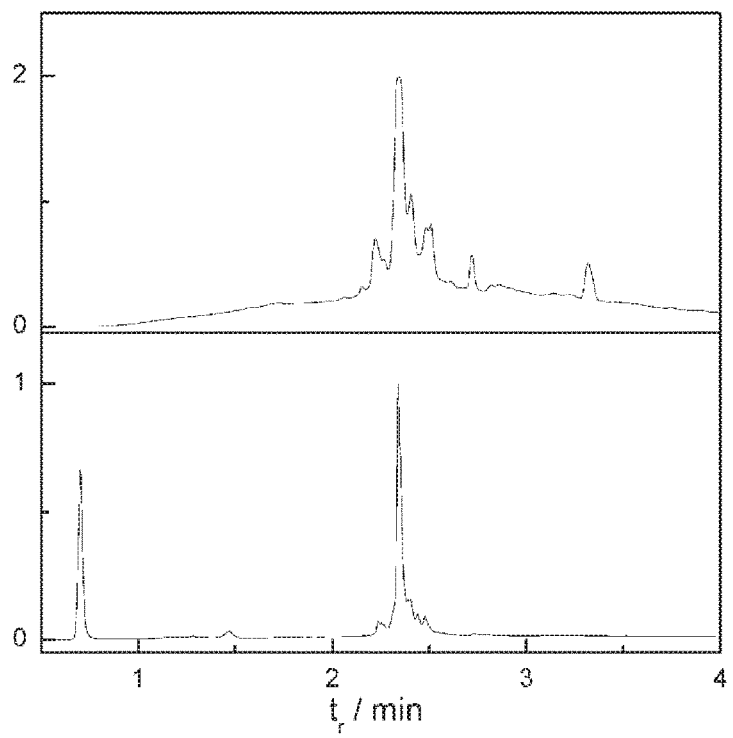
Figure 4:
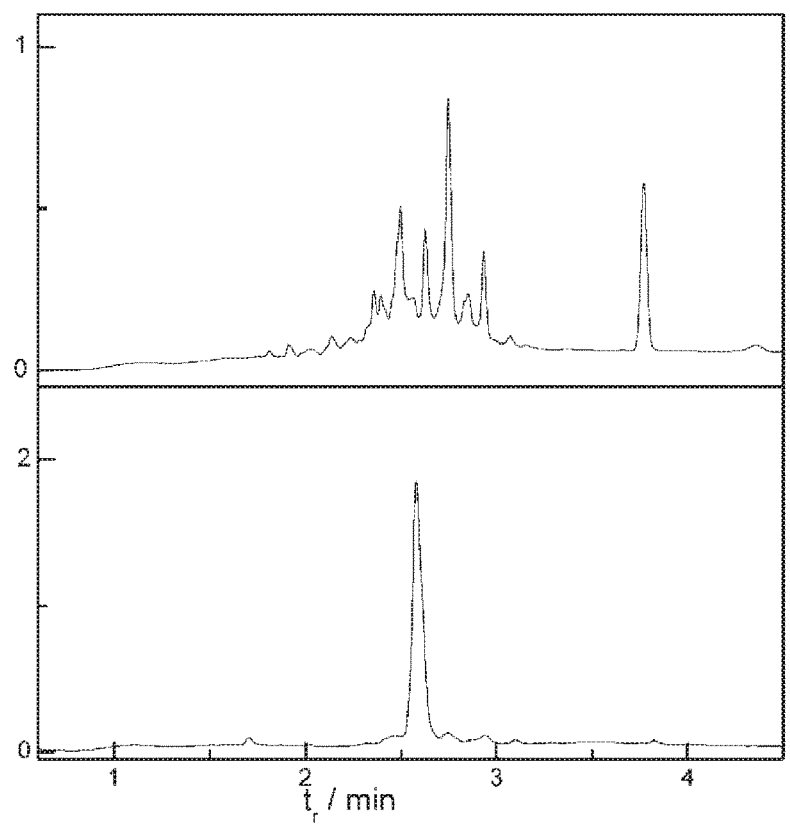
Figure 4:
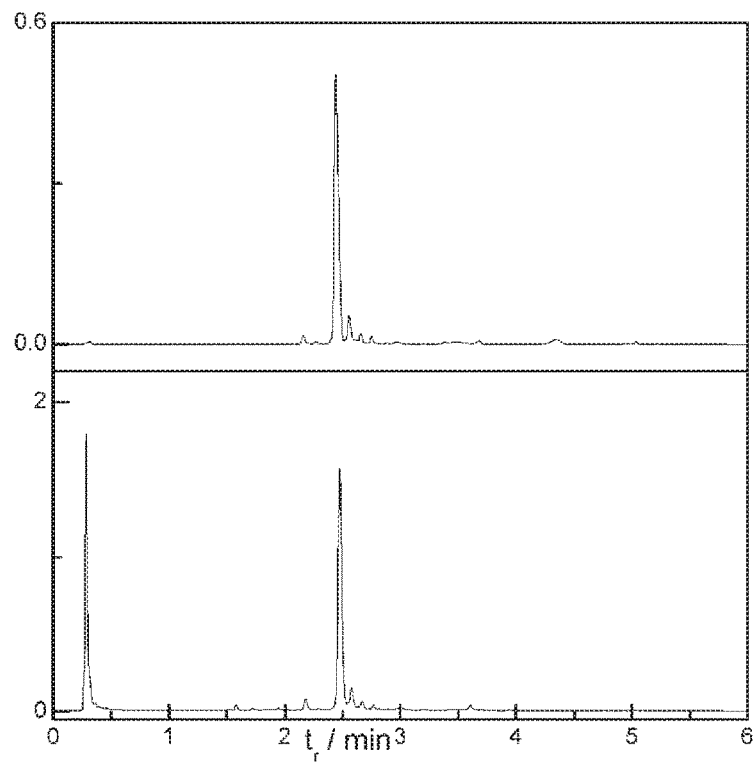
Figure 4:
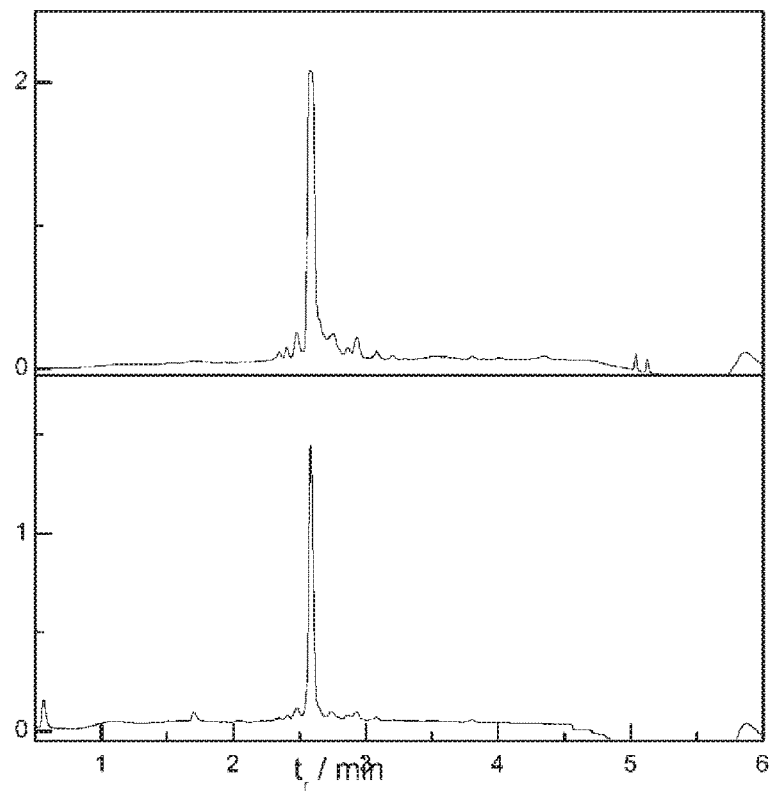
Figure 4:
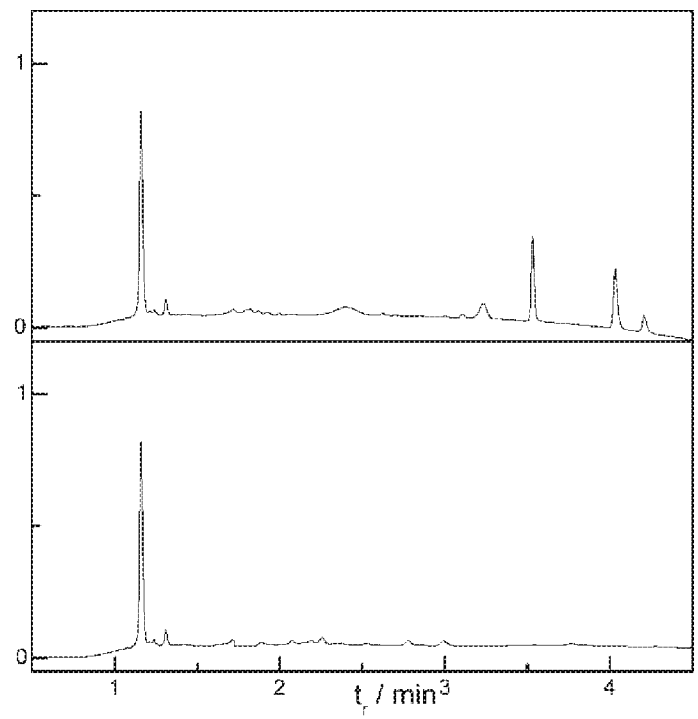
Figure 4:
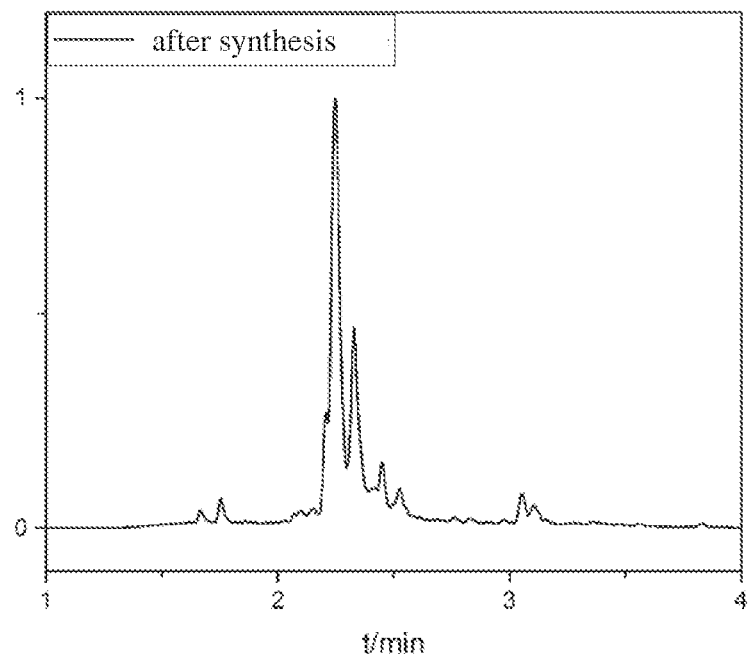
Figure 4:
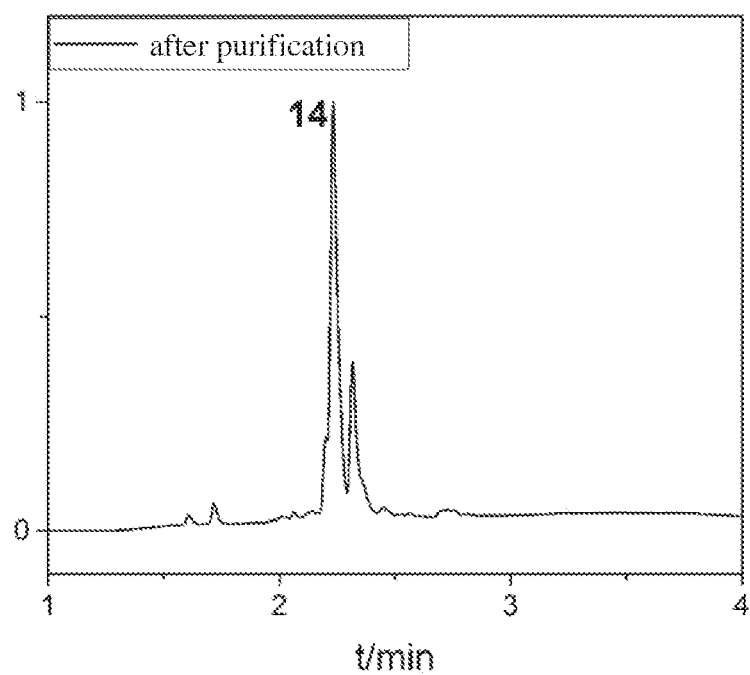
Figure 5:
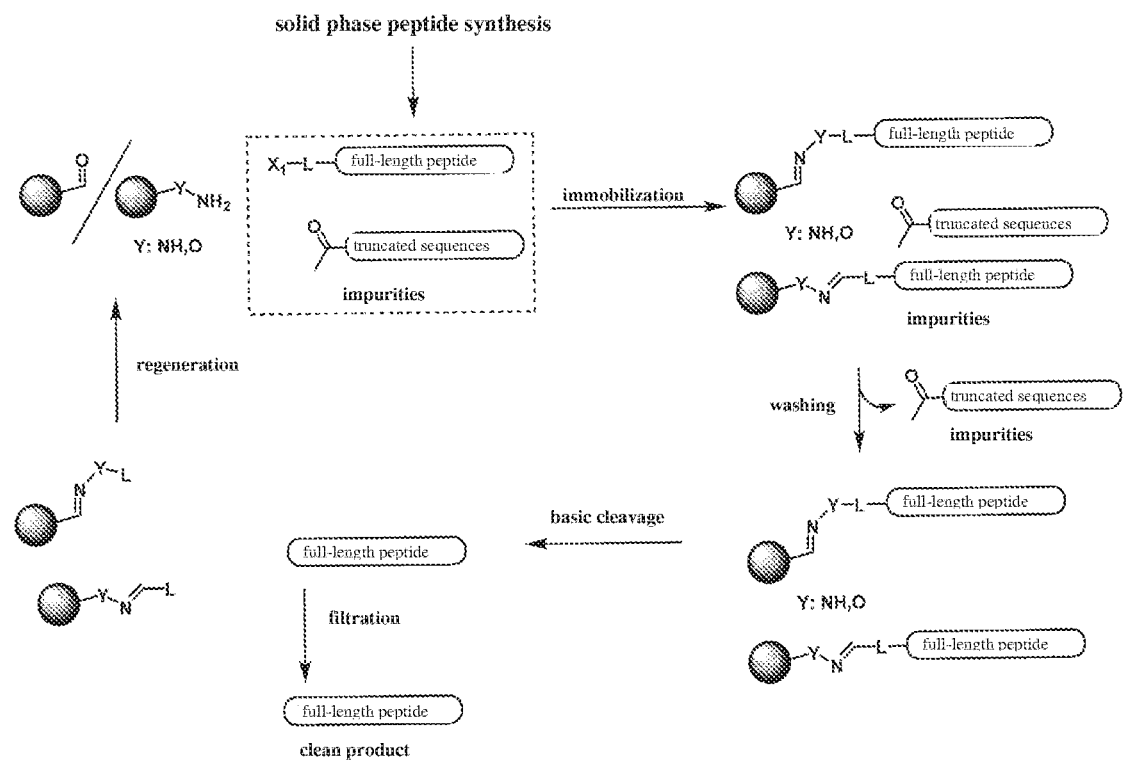
FIG. 5 shows a schematic representation of the method according to the invention to illustrate the same.

The purity of the individual phases was assessed by means of the UPLC-MS. The chromatograms of the non-purified (without capture molecule FM) and purified peptides as well as of the supernatant that contained the impurities are shown in FIG. 4. A peptide purity of 85% (originally 39%) was achieved for 7, of 93% (originally 39%) was achieved for 8, of 80% (originally 24%) was achieved for 9, of 90% (originally 23%) was achieved for 10, of 87% (originally 60%) was achieved for 11, of 90% (originally 40%) was achieved for 12, of 95% (originally 37%) was achieved for 13 (see FIG. 4).

TABLE 2

Purity and yield of different peptides after application of the purification meethod according to the invention

| Name | No. | Application | Status | Length in aa | Hydrophobic aa | Purity crude product | Purity after treatment | Yield |
|---|---|---|---|---|---|---|---|---|
| Tau1 | 7 | Alzheimer's disease | preclinical | 13 | 62% | 40% | 85% | 70% |
| Tau2 | 8 | Alzheimer's disease | preclinical | 12 | 58% | 39% | 93% | 69% |
| GNRH | 9 | fertilisation | approved | 32 | 59% | 35% | 80% | 42% |
| Magainine | 10 | antibiotic | approved | 23 | 65% | 23% | 90% | 62% |
| Terts72Y | 11 | lung cancer | phase II | 9 | 77% | 60% | 87% | 92% |
| Bivalrudin | 12 | anti-coagulation | approved | 20 | 65% | 40% | 90% | 89% |
| TAT | 13 | HIV | phase II | 12 | 17% | 37% | 95% | 83% |
| Testpeptid | 14 | research | — | 13 | 46% | 45% | 60% | — |

Figure 10:
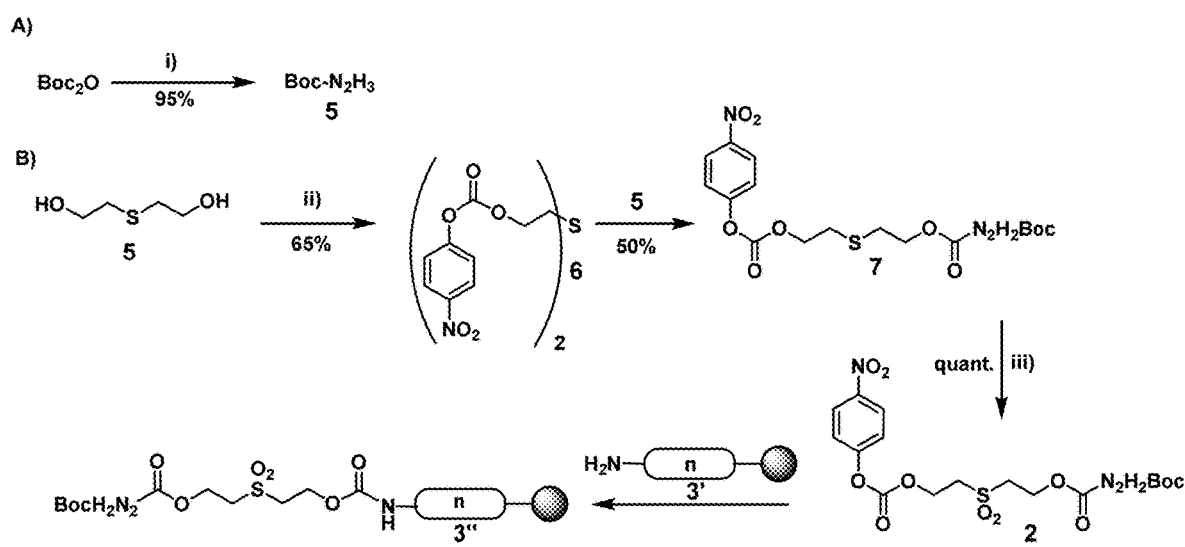
FIG. 10 shows Scheme 7: Synthesis of the base-labile linker i) $N_2H_4*H_2O$; ii) 2.2 eq. $pNO_2PhCO_2Cl$; iii) mCPBA; n: peptide.

The synthesis of the base-labile linker 2 was performed according to scheme 7 in FIG. 10.

Materials and Methods

Solid Phase Peptide Synthesis and Purification

The automated solid phase peptide synthesis was performed in 25 µmol batches with a MultiPep RS peptide synthesis machine from Intavis AG. The syntheses of peptide amides were performed on Tentagel R RAM resin (0.2 mmol-g-1) from Rapp Polymer. Before the beginning of the synthesis, the resin was transferred to 3 mL syringe reactors (PE reactor from Multisyntech) and soaked in DMF. Unless otherwise specified, the specification of equivalents refers to the initial loading of the resin used.

Fmoc-Removal:

To remove the temporary Fmoc protecting groups, the resin was treated once for 4 min and once for 6 min with 400 L piperidine/DMF (4:1) and subsequently washed five times with 800 L DMF and it was continued with the coupling of the Fmoc amino acid derivatives.

Coupling of Fmoc Amino Acid Derivatives:

A solution of 5 eq. amino acid in DMF (0.3 M) was pre-activated for 1 min at room temperature with solutions of 4.5 eq. HCTU in DMF (0.3 M) and 10 eq. NMM in DMF (0.6M) and then added to the resin. After 30 min reaction time, the resin was washed three times with 800 µL DMF and it was continued with blocking the termination sequences.

Blocking the Truncated Sequences:

The resin was treated once for 5 min with 400 µl $AC_2O$/2,6-Lutidin/DMF solution (5:6:89) and subsequently washed three times with 800 µL DMF each.

Last Step Coupling of the Capture Molecule:

As the last step of the solid phase peptide synthesis, the capture molecule 2 was coupled to the desired target peptide. The synthesis resin was mixed with a solution of 5 eq. capture molecule 2 in DMF (0.3 M) and 5 eq. Oxyma in DMF (0.3 M) and 12 eq. DIPEA in DMF (0.7 M) mixed. After 60 min reaction time, it was washed twice with 800 µL DMF each.

Release from Polymeric Support:

The resin was with 2 mL of a solution of 96% TFA, 2% water, 2% triisopropylsilane, in the case of thiol-containing amino acids (cysteine or methionine) in the target sequence 0.5% ethandithiol and 0.5% thioanisole were added to the solution, wherein the amount of TFA was reduced by 1%. The synthesis resin was treated with this cleaving mixture and shaken for 2 h at room temperature. Afterwards, the cleaving solution was collected and the resin was washed twice with 1 mL TFA each. The cleaving solution was combined with the washing solutions and precipitated in 50 ml cold diethyl ether. This suspension was then centrifuged and the organic supernatant was discarded.

Immobilization on Purification Resin:

After centrifugation, the crude precipitate was dissolved in 3 ml of the conjugation buffer (0.1 M $NH_4OAc$, 0.1 M aniline, pH=3), if the mixture did not dissolve completely, acetonitrile was added. This solution was transferred into a 6 ml syringe from bBraun with a filter insert PE 25 m pore size from Multisyntech, in this syringe was one gram functionalized sepharose. Immobilization was performed for 30 to 60 minutes. It was then washed 5 times with deionized water of MilliQ purity, 5 times with a 4M urea solution and 5 times with water. Then the desired peptide was cleaved basically with 5 v % $NH_4OH$ and 1 v % mercaptoethanol in water from the resin. Lyophilization provided the desired peptides as a white flaky solid.

Synthesis of Capture Molecule 2 (Compound 2 in Scheme 7—Corresponds to Compound (25))

Tert-butylhydrazine Carboxylate 5 (Compound 5 in Scheme 7)

Hydrazine monohydrate (80%, 32.5 g, 520 mmol) was mixed with isopropanol (100 ml) at 0° C., with a solution of $Boc_2O$ (50.0 g, 230 mmol) in isopropanol (50 ml) drop by drop. The reaction mixture became turbid after addition and stirring was continued at room temperature for 2 h. The solvent was removed, the residue dissolved in dichloromethane and dried over magnesium sulphate. Then the solvent was evaporated and the residue was recrystallized from hexane, resulting in the title compound 5 (22.8 g, 75%) as colorless crystals. Smp 36-37° C. Rf (EtOAc/hexane 1:1) 0.20. $^1$H-NMR (300 MHz, $CDCl_3$): δ 6.16 (s, 1H, NH), 3.67 (s, 2H, $NH_2$), 1.42 (s, 9H, $C(CH_3)_3$). $^{13}$C-NMR (75 MHz, $CDCl_3$, TMS): δ 158.3, 77.2.28.5. The analytical data are consistent with the literature data (A. Bredihhin, U. Maeorg, Tetrahedron 2008, 64, 6788-6793).

Bis(4-nitrophenyl)(thiobis(ethane-2,1-diyl))bis(carbonate) 6 (Compound 6 in Scheme 7)

6.72 (33 mmol) 4-nitrophenyl chloroformate was added to a solution of 1.87 ml (2.12 g, 15 mmol) 2,2-thiodiethanol in 40 ml anhydrous dichloromethane. Then 2.68 ml (33 mmol) of anhydrous pyridine was slowly added drop by drop with ice cooling and vigorous stirring. The reaction mixture was stirred for 1 h at room temperature. The reaction solution was mixed with 100 ml saturated ammonium chloride solution, extracted three times with 100 ml chloroform and dried over anhydrous magnesium sulphate.

The organic phases were combined and constricted in a vacuum. The residue was absorbed into ethyl acetate and the product was precipitated with a small amount of cyclohexane. After filtration, 5.43 g (12 mmol, 80%) was obtained as white solid. Melting point: 136.5° C., Rf (EtOAc/cyclohexane 1:1) 0.78. $^1$H NMR (300 MHz, DMSO) δ 8.30 (d, J=9.2 Hz, 2H, Ar—H), 7.55 (d, J=9.3 Hz, 2H, Ar—H), 4.42 (t, J=6.4 Hz, 2H, $CH_2$), 2.96 (t, J=6.5 Hz, 2H, $CH_2$). $^{13}$C-NMR (75 MHz, $CDCl_3$, TMS): δ 155.22, 151.93, 145.17, 125.41, 122.56, 67.85, 29.63.

2-[2-(1-((tert-butyl)oxy-carbonyl)oxy-carbonyl)-hydrazyl-ethylsulfanyl]-ethyl 4-nitrophenyl carbonate 7 (Compound 7 in Scheme 7)

1.97 g (4.31 mmol) bis(4-nitrophenyl) (thiobis(ethane-2,1-diyl))bis(carbonate) 6 were added to 20 ml dry dichloromethane and at 0° C. 1 eq. (0.58 g, 4.31 mmol) tert-butyl hydrazine carboxylate 5 with 3 eq. (1.13 ml, 6.66 mmol) DIPEA was slowly added dropwise for one hour. The reaction solution was stirred for another 12 hours and then mixed with water. The product was extracted three times with 100 ml dichloromethane and dried over anhydrous magnesium sulphate. The organic phases were combined and constricted in a vacuum. The residue was purified by column chromatography (EtOAc/cyclohexane 2:1), after which 1.03 g (2.31 mmol, 53%) of a transparent oil was obtained. Rf (EtOAc/Cyc10hexane 1:1) 0.20. $^1$H NMR (300 MHz, CDCh) δ 8.28 (d, J=9.1 Hz, 2H, Ar—H), 7.39 (d, J=9.1 Hz, 1H, Ar—H), 6.64 (s, 1H, NH), 6.33 (s, 1H, NH), 4.44 (t, J=6.8 Hz, 2H, $CH_2$), 4.33 (t, J=6.6 Hz, 2H, $CH_2$), 2.92 (t, J=6.8 Hz, 2H, $CH_2$), 2.84 (t, J=6.6 Hz, 2H, $CH_2$), 1.46 (s, 9H). $^{13}$C NMR (75 MHz, $CDCl_3$) δ 155.52, 152.57, 125.47, 121.96, 82.09, 68.06, 65.34, 64.18, 31.10, 30.59, 28.27, 27.03.

2-[2-(1-((tert-butyl)oxy-carbonyl)oxy-carbonyl)-hydrazyl-ethylsulfonyl]-ethyl4-nitrophenyl carbonate 2 (Compound 2 in Scheme 7)

To a solution of thioether 7 (0.52 g, 1.1 mmol) in 50 ml dichloromethane, 77% (489 g, 2.2 mmol) of m-CPBA was slowly added at room temperature. After stirring for 12 h the reaction mixture was mixed with 1M $NaHCO_3$ solution and the organic phase was extracted three times with 50 ml dichloromethane. The combined organic phases were dried with magnesium sulphate and the solvent was removed from the rotary evaporator, after which the product was precipitated as white amorphous solid 0.52 mg (1.1 mmol, quantitative). $^1$H NMR (300 MHz, $CDCl_3$) δ 8.29 (d, J=9.2 Hz, 2H, Ar—H), 7.41 (d, J=9.2 Hz, 2H, Ar—H), 6.89 (s, 1H, NH), 6.36 (s, 1H, NH), 4.74 (t, J=5.9 Hz, 2H, $CH_2$), 4.63 (t, J=5.3 Hz, 2H, $CH_2$), 3.54 (t, J=5.9 Hz, 2H, $CH_2$), 3.45 (t, J=5.5 Hz, 2H, $CH_2$), 1.45 (s, 9H). $^{13}$C NMR (75 MHz, CDl3) δ 155.85, 155.18, 152.29, 145.79, 125.56, 122.00, 82.32, 62.25, 59.45, 54.01, 53.24, 28.23.

The synthesis of the compounds according to formula (14), (15), (17), (18), (19): was based on a modular principle, which is shown in the general synthesis scheme (Scheme 1).

Syntheses for the Preparation of the Compound of Formula (14)

N,N'-Bis-(tert-butoxycarbonyl)-aminooxyacetyl-N-hydroxylsuccinimide Ester (BS2: X=O, $R^1$=Boc)

Add N-hydroxylsuccinimide (0.41 g, 3.20 mmol) and dicyclohexylcarbodiimide (0.67 g, 0.32 mmol) at 0° C. to a solution of commercially available N,N'-bis-boc-aminooxyacetic acid (1.00 g, 3.20 mmol) in 11 ml ethyl acetate/dioxane (1:1). At room temperature the solution was allowed to stir for 3 hours and the suspension was filtered over Celite and washed with ethyl acetate. The filtrate was concentrated under vacuum to dry and dissolved again in 100 ml ethyl acetate. It was washed with 5% $NaHCO_3$ solution, saturated NaCl solution and water (100 ml each). The organic phase was dried with $MgSO_4$ and evaporated under vacuum wherein 1.24 g (3.20 mmol) product was obtained as a white solid. Yield: 1.24 g (quant.); Rf (cyclohexane/ethyl acetate, 1:1) 0.50; $^1$H NMR (300 MHz, $CDCl_3$) δ 4.86 (s, 2H), 2.85 (s, 4H), 1.53 (s, 18H).

N,N'-Bis-(tert-butoxycarbonyl)-aminooxyacetyl-1-((2-aminoethyl)thio)propan-2-ol amide (BS3: X=O, $R^1$=Boc)

BS2 (X=O, $R_1$=Boc, 1.00 g, 2.55 mmol) was mixed in 25 ml dichloromethane with 1-((2-aminoethyl)thio)propan-2-ol (0.38 g, 2.55 mmol) and diisopropyl-ethylamine (DIPEA, 0.53 ml, 3.06 mmol) and stirred overnight. It was washed with 5% $NaHCO_3$ solution, saturated NaCl solution and water (100 ml each). The organic phase was dried with $MgSO_4$ and vacuum-constricted wherein 1.04 g (2.55 mmol) product was obtained as a white solid. Yield: 1.04 g (quant.); Rf ($CH_2Cl_2$/MeOH, 98:2) 0.35; $^1$H NMR (300 MHz, $CDCl_3$) δ 7.95 (s, 1H), 4.44 (s, 2H), 3.92-3.82 (m, 1H), 3.53 (qd, J=6.7, 1.5 Hz, 2H), 2.83-2.65 (m, 4H), 2.49 (dd, J=13.7, 8.7 Hz, 1H), 1.55 (s, 18H), 1.25 (d, J=6.2 Hz, 3H); $^{13}$C NMR (75 MHz, $CDCl_3$) δ 167.94, 150.57, 85.41, 65.98, 41.86, 38.81, 32.21, 28.19, 22.23.

2,2-Dimethylpropanoyloxy-[2-[2-[2-[2-(4-nitrophenoxy)carbonyloxypropylthionyl]ethylamino]-2-oxo-ethoxy]amino] 2,2-dimethylpropanoate P' (X=O, $R_1$=Boc, $R_2$=$OC_6H_4pNO_2$)

Bis(4-nitrophenyl)carbonate (1.01 g, 4.95 mmol) were added to a solution of BS3 (X=O, $R_1$=Boc) (1.52 g, 3.30 mmol) in 5 ml dry $CH_2Cl_2$. Dry pyridine (0.40 ml, 4.95 mmol) was then added under ice cooling. The reaction solution was stirred for 18 hours. The precipitate was filtered off and was washed with 50 ml DCM. The filtrate was washed with saturated $NH_4Cl$ solution (50 ml) and the aqueous phase was extracted with 50 ml $CHCl_3$. After drying with $MgSO_4$, the combined organic phases were constricted on the rotary evaporator and the residue was purified by column chromatography (cyclohexane/etOAc, 2:1). Yield: 1.27 g (67%); Rf (cyclohexane/etOAc, 1:1) 0.44; $^1$H NMR (300 MHz, $CDCl_3$) δ 8.27 (d, J=9.2 Hz, 2H), 7.89 (s, 1H), 7.39 (d, J=9.2 Hz, 2H), 5.00 (dd, J=12.5, 6.3 Hz, 1H), 4.43 (s, 2H), 3.53 (dd, J=13.3, 6.5 Hz, 1H), 2.86-2.69 (m, 2H), 1.53 (s, 18H), 1.47 (d, J=6.3 Hz, 3H).

2,2-Dimethylpropanoyloxy-[2-[2-[2-(4-nitrophenoxy)carbonyloxypropylsulfonyl]ethylamino]-2-oxo-ethoxy]amino]2,2-dimethylpropanoates Formula (14)

Slowly add m-CPBA (0.96 g, 4.30 mmol) at room temperature to a solution of P' (X=O, $R_1$=Boc, $R_2$=OC$_6$H$_4$pNO$_2$) (1.27 g, 2.15 mmol) in 21 ml dichloromethane. After 12 hours of stirring, the reaction mixture was washed twice with a saturated NaHCO$_3$ solution (15 ml) and the organic phase was concentrated in a vacuum after drying with MgSO$_4$. The sulfone was preserved as a white solid. Yield: 1.26 g (97%); Rf (cyclohexane/etOAc, 1:1) 0.29; $^1$H NMR (300 MHz, CDCl$_3$) δ 8.28 (d, J=9.3 Hz, 1H), 8.15 (t, J=5.8 Hz, 1H), 7.41 (d, J=9.3 Hz, 1H), 5.48-5.39 (m, 1H), 4.44 (s, 1H), 3.83 (dd, J=6.2, 4.2 Hz, 1H), 3.56 (dd, J=14.9, 8.3 Hz, 1H), 3.37 (t, J=6.5 Hz, 1H), 3.27 (dd, J=14.9, 3.9 Hz, 1H), 1.57 (d, J=6.4 Hz, 1H), 1.54 (s, 7H). $^{13}$C NMR (75 MHz, CDCl$_3$) δ 168.58, 155.42, 151.58, 150.52, 145.67, 125.46, 122.04, 85.60, 77.16, 76.62, 70.63, 58.19, 53.67, 33.07, 28.16, 20.21; ESI-MS: (calculated MNa$^+$: 628.16 g/mol, found: 628.17 m/z).

Syntheses for the Preparation of the Compound of Formula (18)

((tert-butoxycarbonyl)amino)glycine (BS1 X=NH, R$_1$=H)

Bromoacetic acid (1.48 g, 10.4 mmol) was added to a methanolic solution (10 ml) of NaOH (0.70 g, 17.4 mmol) and Boc-hydrazine (1.17 g, 8.7 mmol) at 0° C. The solution was heated for 5 hours under reflux. Then MeOH was removed and 50 ml water was added. The aqueous phase was extracted three times with ethyl acetate (50 ml). The aqueous phase was then brought to pH 2 with citric acid and extracted three times with 50 ml ethyl acetate. The combined organic phases were dried with MgSO$_4$ and the solvent was removed under reduced pressure. Yield: 0.85 g (51%) white solid; Rf (CH$_2$Cl$_2$/MeOH, 8:2) 0.15. $^1$H NMR (300 MHz, DMSO) δ 8.55 (s, 2H), 8.17 (s, 2H), 3.40 (s, 2H), 1.37 (s, 9H); ESI-MS: (calculated MH+: 191.10 g/mol, found: 191.33 m/z).

N-(tert-butoxycarbonyl)-N-((tert-butoxycarbonyl)amino)glycine (BS1 X=NBoc, R$_1$=H)

Boc$_2$O (5.74 g, 26.03 mmol) was added as a solid to a solution of ((tert-butoxycarbonyl)amino)glycine (5.00 g, 26.0 mmol) and NaOH (1.57 g, 39.04 mmol) in 104 ml dioxane/H$_2$O (1:1). The solution was stirred overnight at room temperature for 18 hours and the dioxane was then removed under reduced pressure. Add 100 ml saturated NaHCO$_3$ solution to the aqueous residue and wash twice with 100 ml Et$_2$O. The aqueous phase was brought to pH 2 with citric acid. The white suspension was extracted three times with 150 ml ethyl acetate. After drying with MgSO4 the solvent was removed wherein a white solid formed. Yield: 7.56 g (quant.); Rf (CH$_2$Cl$_2$/MeOH, 9:1) 0.75; $^1$H NMR (300 MHz, DMSO) δ 12.34 (s, 1H), 9.24 (s, 1H), 3.56 (s, 2H), 1.46-1.32 (m, 18H).

N-(tert-butoxycarbonyl)-N-((tert-butoxycarbonyl)amino)glycinyl-N-hydroxylsuccinimide (BS2 X=NBoc, R$_1$=H)

N-(tert-butoxycarbonyl)-N-((tert-butoxycarbonyl)amino) glycine (1.36 g, 4.45 mmol) in 15 ml ethyl acetate/dioxane (1:1) was added at 0° C. to N-hydroxylsuccinimide (0.52 g, 4.45 mmol) and dicyclohexylcarbodiimide (DCC, 0.93 g, 4.45 mmol). At room temperature, the solution was allowed to stir for 15 hours. Afterwards the suspension was filtered over Celite and washed with ethyl acetate. The filtrate was concentrated under vacuum to dry and dissolved again in 100 ml ethyl acetate. It was washed with 5% NaHCO$_3$ solution, saturated NaCl solution and water (100 ml each). The organic phase was dried with MgSO$_4$ and evaporated under vacuum wherein 1.24 g (3.20 mmol) product was obtained as white foam. Yield: 1.51 g (88%); Rf (cyclohexane/ethyl acetate, 1:1) 0.45; $^1$H NMR (300 MHz, CDCl$_3$) δ 4.67 (s, 1H), 4.19 (s, 2H), 2.87 (s, 4H), 1.49 (m, 18H).

N-(tert-butoxycarbonyl)-N-((tert-butoxycarbonyl)amino)glycinyl-1-((2-aminoethyl)thio)propan-2-ol Amide (BS3: X=NBoc, R$_1$=H)

BS2 (X=NBoc, R$_1$=H, 0.36 g, 0.92 mmol) was mixed in 10 ml dichloromethane with 1-((2-aminoethyl)thio)propan-2-ol (0.13 g, 0.92 mmol) and DIPEA (0.18 ml, 1.01 mmol) and stirred overnight. It was washed with 5% NaHCO$_3$ solution, saturated NaCl solution and water (100 ml each).
The organic phase was dried with MgSO$_4$ and vacuum-constricted wherein 0.27 g (0.65 mmol) product was obtained as white foam. Yield: 0.27 g (quant.); Rf (CH$_2$Cl$_2$/MeOH, 98:2) 0.36; $^1$H NMR (300 MHz, CDCl3) δ 8.34 (s, 1H), 6.66 (s, 1H), 4.05 (s, 2H), 3.90-3.81 (m, 1H), 3.49 (dd, J=10.4, 4.0 Hz, 2H), 2.78-2.63 (m, 3H), 2.47 (dd, J=13.7, 8.7 Hz, 1H), 1.49 (s, 9H), 1.46 (s, 9H), 1.23 (d, J=6.2 Hz, 3H).

[2-(2,2-dimethylpropanoyloxy)-2-[2-[2-[2-(2,5-dioxopyrrolidin-1-yl)oxycarbonyloxypropylthionyl]ethylamino]-2-oxo-ethyl]hydrazino] 2,2-dimethylpropanoate P' (X=O, R$_1$=Boc, R$_2$=ONO$_2$C$_2$H$_4$)

N,N-disuccinimidyl carbonate (0.19 g, 0.72 mmol) was added to a solution of BS3 (X=NBoc, R$_1$=H) (0.25 g, 0.72 mmol) in 5 ml dry CH$_2$Cl$_2$. Dry pyridine (0.06 ml, 0.73 mmol) was then added under ice cooling. The reaction solution was stirred for 17 hours. 50 ml DCM was added to the solution. The organic phase was washed with 10% citric acid solution and dried with MgSO$_4$. The combined organic phases were constricted at the rotary evaporator and the residue was purified by column chromatography (CH$_2$Cl$_2$/MeOH, 19:1). Yield: 1.27 g (67%); Rf (CH$_2$Cl$_2$/MeOH, 9:1) 0.60; $^1$H NMR (300 MHz, CDCl$_3$) δ 8.53 (d, J=95.5 Hz, 1H), 7.07 (s, J=9.0 Hz, 1H), 4.01 (s, 2H), 3.82 (ddd, J=8.2, 6.1, 3.9 Hz, 1H), 3.41 (d, J=6.1 Hz, 4H), 2.67 (dt, J=13.2, 9.3 Hz, 4H), 2.46 (dd, J=13.7, 8.2 Hz, 2H), 1.44 (s, 9H), 1.41 (s, 9H), 1.18 (t, J=6.8 Hz, 3H). $^{13}$C NMR (75 MHz, CDCl$_3$) δ 169.71, 162.47, 154.43, 77.16, 66.04, 50.53, 41.57, 39.13, 32.22, 28.18, 28.12, 25.57, 22.06, 18.88.

[2-(2,2-dimethylpropanoyloxy)-2-[2-[2-[2-(2,5-dioxopyrrolidin-1-yl)oxycarbonyloxypropylsulfonyl]ethylamino]-2-oxo-ethyl]hydrazino] 2,2-dimethylpropanoate (formula (18))

m-CPBA (0.81 g, 0.36 mmol) was slowly added at room temperature to a solution of P' (X=NBoc, R$_1$=H, R$_2$=ONO$_2$C2H$_4$) (0.10 g, 0.18 mmol) in 5 ml dichloromethane. After stirring for 14 hours, the reaction mixture was washed three times with 5% NaHCO$_3$ in a saturated NaCl solution (33 ml each) and the organic phase was then dried with MgSO$_4$. The solvent was removed in a vacuum and the sulfone was preserved as a white amorphous solid. Yield: 0.08 g (76%); Rf (CH$_2$Cl$_2$/MeOH, 9:1) 0.45 1H NMR (300 MHz, CDCl$_3$) δ 8.48 (s, 1H), 6.95 (s, 1H), 4.39 (dt, J=15.7, 7.8 Hz, 1H), 4.06 (s, 2H), 3.73 (d, J=4.3 Hz, 2H), 3.48-3.17 (m, 4H), 3.41 (d, J=6.1 Hz, 2H), 3.02 (d, J=13.2 Hz, 1H), 2.85-2.68 (m, 3H), 1.48 (s, 9H), 1.43 (s, 9H), 1.30 (d, J=6.4 Hz, 3H); $^{13}$C NMR (75 MHz, CDCl$_3$) δ 170.18, 167.99, 154.71, 133.30, 131.86, 130.13, 129.83, 128.20, 77.16, 62.88, 53.37, 33.53, 28.23, 28.16, 25.57, 23.25. ESI-MS: (calculated MNa+: 603.19 g/mol, found: 603.06 m/z).

Syntheses for the Preparation of the Compound of Formula (15)

N-(tert-butoxycarbonyl)-aminooxyacetyl-1-((2-aminoethyl)thio)propan-2-ol amide (BS3: X=O, $R_1$=H)

Commercially available 2-((((tert-butoxycarbonyl)amino)oxy)acetic acid (1.00 g, 4.73 mmol) was dissolved in dry $CH_3CN$ (47 ml). Add N-hydroxysuccinimide (0.66 g, 5.68 mmol) and DCC (1.18 g, 5.68 mmol) successively to the solution and stir the resulting reaction mixture at room temperature for 1 hour. Then add a solution of 1-((2-aminoethyl)thio)propan-2-ol (0.85 g, 5.68 mmol) in 3 ml dry $CH_3CN$ and stir the resulting reaction mixture at room temperature for 18 hours. The $CH_3CN$ was removed and the concentrate absorbed in 50 ml ethyl acetate. It was washed with 10% citric acid solution (50 ml) and saturated NaCl solution. The residue obtained was purified by chromatography on a silica gel column with a step gradient of MeOH (1-8%) in $CH_2Cl_2$ as a mobile phase. The desired building block was obtained as white foam. Yield: 0.26 g (16%); Rf ($CH_2Cl_2$/MeOH, 9:1) 0.50; $^1$H NMR (300 MHz, acetones) δ 8.14 (s, 1H), 4.22 (s, 2H), 3.85 (t, J=1.6 Hz, 1H), 3.53-3.38 (m, 2H), 2.72-2.66 (m, 2H), 2.62-2.58 (m, 2H), 1.46 (s, 9H), 1.19 (d, J=6.1 Hz, 3H).

[2-[2-[2-(4-nitrophenoxy)carbonyloxypropylthionyl]ethylamino]-2-oxo-ethoxy]amino] 2,2-dimethylpropanoate P' (X=O, $R_1$=H, $R_2$=OC$_6$H$_4$pNO$_2$)

Bis(4-nitrophenyl)carbonate (0.276 g, 0.90 mmol) were added to a solution of BS3 (X=O, $R_1$=H) (0.24 g, 0.75 mmol) in 5 ml dry $CH_2Cl_2$. Dry pyridine (0.07 ml, 0.75 mmol) was then added under ice cooling. The reaction solution was stirred for 18 hours. The precipitate was filtered off and was washed with 50 ml DCM. The filtrate was washed with saturated NH$_4$Cl solution (50 ml) and the aqueous phase was extracted with 50 ml CHCl$_3$. After drying with MgSO$_4$, the combined organic phases were constricted on the rotary evaporator and the residue was purified by column chromatography (cyclohexane/etOAc, 2:1). Yield: 0.27 g (96%); Rf (cyclohexane/etOAc, 1:1) 0.34; $^1$H NMR (300 MHz, CDCl$_3$) δ 8.35 (s, 1H), 8.27 (d, J=9.1 Hz, 2H), 7.58 (s, 1H), 7.40 (d, J=9.1 Hz, 2H), 5.06-4.94 (m, 1H), 4.32 (s, 2H), 3.54 (d, J=6.3 Hz, 2H), 2.87-2.73 (m, 4H), 1.48 (d, J=4.1 Hz, 3H), 1.47 (s, Hz, 9H).

[2-[2-[2-(4-nitrophenoxy)carbonyloxypropylsulfonyl]ethylamino]-2-oxo-ethoxy]amino] 2,2-dimethylpropanoates Formula (15)

m-CPBA (0.263 g, 1.18 mmol) was slowly added at room temperature to a solution of P' (X=O, $R_1$=Boc, $R_2$=OC$_6$H$_4$pNO$_2$) (0.30 g, 0.59 mmol) in 5 ml dichloromethane. After 12 hours of stirring, the reaction mixture was washed twice with a saturated NaHCO$_3$ solution (15 ml) and the organic phase was concentrated in a vacuum after drying with MgSO$_4$. The sulphone was preserved as white foam. Yield: 0.250 g (84%); Rf (cyclohexane/etOAc, 1:1) 0.05; 1H NMR (300 MHz, CDCl3) δ 8.51 (s, 1H), 8.28 (d, J=9.2 Hz, 2H), 7.64 (s, 1H), 7.41 (d, J=9.2 Hz, 3H), 5.47-5.35 (m, 1H), 4.33 (s, 2H), 3.88-3.79 (m, 2H), 3.57 (dd, J=14.9, 8.3 Hz, 1H), 3.41-3.34 (m, 2H), 3.28 (dd, J=14.8, 3.8 Hz, 1H), 1.57 (d, J=6.4 Hz, 3H), 1.48 (s, 9H); $^{13}$C NMR (75 MHz, CDCl$_3$) δ 168.58, 155.42, 151.58, 150.52, 145.67, 125.46, 122.04, 85.60, 77.16, 76.62, 70.63, 58.19, 53.67, 33.07, 28.16, 20.21; ESI-MS: (calculated MH+: 528.16 g/mol, found: 528.15 m/z).

Syntheses for the Preparation of the Compound of Formula (16)

Sodium 4-carboxy-2-nitrobenzenesulfonate 4-sulfamylbenzoic acid was dissolved in a mixture of 5 ml fuming HNO$_3$ and 10 ml H$_2$SO$_4$ (95%). The reaction solution was stirred overnight at 90° C. and then diluted with 100 ml water. At 0° C. the acid was neutralized by adding Na$_2$CO$_3$. Subsequently, acidification was carried out by adding HCl until the pH value was 2. The water was removed and the residue was extracted with EtOH/iPrOH (1:1). Subsequently, the organic solvent was removed wherein the product was obtained as a brown solid. Yield: 6.86 g (61%); Rf (CH$_2$Cl2/MeOH/AcOH, 7:2:1) 0.05; 1H NMR (300 MHz, MeOD) δ 8.23 (d, J=1.6 Hz, 1H), 8.17 (d, J=1.6 Hz, 1H), 8.16 (s, 1H); ESI-MS (neg.): (calculated (M-Na)—: 245.97 g/mol, found: 296.00 m/z).

Sodium 4-(2-(tert-butoxycarbonyl)hydrazine-1-carbonyl)-2-nitrobenzenesulfonate

A solution of t-butyl carbazate (1.91 g, 14.27 mmol) and sodium 4-carboxy-2-nitrobenzenesulfonate (3.84 g, 14.27 mmol) and 1-ethyl-3-(3-dimethylaminopropyl)carbodiimide (2.76 g, 14.27 mmol) was mixed overnight at room temperature in 60 ml methanol/H$_2$O (1:1). The solvents were removed under reduced pressure and the residue was purified by column chromatography (CH$_2$Cl$_2$/MeOH, 9:1). A solution of t-butyl carbazate (1.91 g, 14.27 mmol) and sodium 4-carboxy-2-nitrobenzenesulfonate (3.84 g, 14.27 mmol) and 1-ethyl-3-(3-dimethylaminopropyl)carbodiimide (2.76 g, 14.27 mmol) was mixed overnight at room temperature in 60 ml methanol/H$_2$O (1:1). The solvents were removed under reduced pressure and the residue was purified by column chromatography (CH$_2$Cl2/MeOH, 9:1). Yield: 6.86 g (61%); Rf (CH$_2$Cl2/MeOH/AcOH, 7:2:1) 0.30; $^1$H NMR (300 MHz, DMSO) δ 10.46 (s, 1H), 9.04 (s, 1H), 8.01 (d, J=1.5 Hz, 1H), 7.99 (d, J=1.5 Hz, 1H), 7.96 (s, 1H), 1.43 (s, 9H); ESI-MS (neg.): (calculated (M-Na)—: 360.05 g/mol, found: 360.00 m/z).

tert-butyl 2-(4-(chlorosulfonyl)-3-nitrobenzoyl)hydrazine-1-carboxylate

Cyanuric chloride (0.26 g, 1.42 mmol) was added to a solution of sodium 4-(2-(tert-butoxycarbonyl)hydrazine-1-carbonyl)-2-nitrobenzenesulfonate (0.55 g, 1.42 mmol) and 18-crown-6 ether (0.02 g, 0.07 mmol) in dry acetone. The solution was heated for 18 h under reflux. After cooling, the reaction mixture was filtered over Celite and purified by column chromatography (CH$_2$Cl$_2$/MeOH, 9:1). Yield: 0.23 g (43%); $^1$H NMR (300 MHz, CDCl$_3$) δ 10.18 (s, 2H), 8.22 (d, J=0.5 Hz, 1H), 8.22 (dd, J=1.7, 0.5 Hz, 1H), 8.18 (d, J=1.6 Hz, 1H), 8.15 (d, J=0.6 Hz, 1H), 1.23 (s, 9H); ESI-MS (neg.): (calculated (M)–: 379.02 g/mol, found: 378.92 m/z).

Syntheses for the Preparation of the Compound of Formula (20)

6-Azidoisobenzofuran-1(3H)-on

A clear solution of 6-amino-phtalid (2.50 g, 15.92 mmol) in 1M HCl (28 ml) was cooled to 0° C. and mixed with 3 ml of an aqueous solution of $NaNO_2$ (1.66 g, 13.89 mmol) drop by drop. The resulting suspension was stirred for 10 min at 0° C. and mixed with 10 ml of a solution of $NaN_3$ (2.09 g, 31.85 mmol) drop by drop at 0° C. (strong $HN_3$ gas development!, foaming). The foamy suspension was stirred at 0° C. for one hour. The precipitate was sucked off and washed several times with a total of 300 ml of water. The brown solid was crushed and dried overnight in a drying cabinet. It was then dissolved in 300 ml $CH_2Cl_2$ and filtered off. The filtrate was freed under vacuum from the solvent wherein a light brown solid was obtained. Yield: 2.53 g (91%); Rf ($CH_2Cl2/MeOH/AcOH$, 7:2:1) 0.30; $^1H$ NMR (300 MHz, $CDCl_3$) δ 7.58 (d, J=1.9 Hz, 1H), 7.47 (dd, J=8.2, 0.7 Hz, 1H), 7.31 (dd, J=8.2, 2.1 Hz, 1H), 5.31 (s, 2H); ESI-MS: (calculated $(MH)^+$: 176.05 g/mol, found: 176.23 m/z).

5-azido-2-(hydroxymethyl)benzohydrazide

6-Azidoisobenzofuran-1(3H)-on (0.50 g, 2.83 mmol) were dissolved in 6 ml dimethylformamide (DMF) and hydrazine hydrate (0.71 ml, 14.13 mmol) was added and the solution was stirred at 70° C. for 3 hours. The DMF and hydrazine hydrate were removed under vacuum. The residue was purified by column chromatography ($CH_2Cl2/MeOH$, 9:1), wherein a light yellow powder was obtained. Yield: 0.10 g (17%). Rf ($CH_2Cl_2/MeOH$, 9:1) 0.53; $^1H$ NMR (300 MHz, DMSO) δ 9.62 (s, 1H), 7.57 (d, J=8.3 Hz, 1H), 7.20 (dd, J=8.3, 2.4 Hz, 1H), 7.09 (d, J=2.4 Hz, 1H), 5.31-5.21 (m, 1H), 4.57 (d, J=5.7 Hz, 2H), 4.50 (s, 2H), 3.33 (s, 2H), ESI-MS: (calculated (MH)+: 208.08 g/mol, found: 207.90 m/z), (calculated $(MNa)^+$: 230.07 g/mol, found: 230.01 m/z).

tert-butyl 2-(5-azido-2-(hydroxymethyl)benzoyl)hydrazine-1-carboxylate

5-Azido-2-(hydroxymethyl)benzohydrazide (0.10 g, 0.48 mmol) were dissolved in Dioxan/EtOAc/iPrOH (1:1:1) 10 ml and mixed with Boc anhydride (0.105 g, 0.48 mmol) and DIPEA (0.10 ml, 0.57 mmol). The solution was stirred at room temperature for 12 hours and then the solvent was removed under reduced pressure. The residue was absorbed in 50 ml $CH_2Cl_2$ and washed twice with a 10% citric acid solution (50 ml each). After drying with $MgSO_4$ and removing the organic solvent, a yellowish oil was obtained. Yield: 0.10 g (67%). Rf ($CH_2Cl_2/MeOH$, 9:1) 0.75; $^1H$ NMR (300 MHz, DMSO) δ 10.06 (s, 1H), 9.04 (d, J=30.3 Hz, 1H), 7.69-7.58 (m, 1H), 7.25 (dd, J=8.3, 2.4 Hz, 1H), 7.10 (d, J=1.3 Hz, 1H), 5.28 (t, J=5.7 Hz, 1H), 4.62 (d, J=5.6 Hz, 2H), 1.43 (s, 9H); ESI-MS: (calculated (MNa)+: 330.12 g/mol, found: 330.29 m/z).

tert-Butyl 2-(5-azido-2-(((((2,5-dioxopyrrolidin-1-yl)oxy)carbonyl)oxy)methyl)benzoyl)hydrazin-1-carboxylate N,N-disuccinimidyl carbonate (0.105 g, 0.41 mmol) was added to a solution of tert-butyl 2-(5-azido-2-(hydroxymethyl)benzoyl)hydrazine-1-carboxylate (0.105 g, 0.34 mmol) in 5 ml dry dimethylformamide. Then dry pyridine (0.03 ml, 0.41 mmol) was added. The reaction solution was stirred for 17 hours at room temperature. The solvent was removed under vacuum. 50 ml DCM was added to the solution. The organic phase was washed with 10% citric acid solution (2×50 ml) and dried with $MgSO_4$. The combined organic phases were constricted at the rotary evaporator and the residue was purified by column chromatography ($CH_2C12/MeOH$, 19:1). Yield: 0.06 g (40%). Rf ($CH_2Cl_2/MeOH$, 19:1) 0.45; $^1H$ NMR (300 MHz, DMSO) δ 10.06 (s, J=10.9 Hz, 1H), 8.99 (s, J=8.4 Hz, 1H), 7.62 (d, J=8.3 Hz, 1H), 7.53 (s, 1H), 7.25 (dd, J=8.3, 2.4 Hz, 1H), 5.76 (s, 2H), 3.34 (s, 4H), 1.43 (s, 9H), ESI-MS: (calculated (MNa)+: 471.12 g/mol, found: 471.25 m/z).

Syntheses for the Preparation of the Compound of Formula (21)

6-Methoxyisobenzofuran-1 (3H)-on

A mixture of 3-methoxybenzoic acid (10.00 g, 65.07 mmol), 37% formalin solution (7.5 ml, 80 mmol), 37% HCl (8.00 ml) and 75 ml 100% acetic acid was heated for 18 hours with reflux. After cooling, the clear solution is switched off and left at this temperature for 14 hours. The acetic acid was removed in the air stream at 80° C. The residue was absorbed in 150 ml toluene and concentrated to 40 ml. The 80° C. hot solution was washed with 40 ml portions of 20% $Na_2CO_3$ solution (3 times) and 40 ml water. After adding 3 ml morpholine, the organic phase was stirred for 2 h at 80° C. and then washed with 50 ml portions of 10% $H_2SO_4$ (3 times) and water. To crystallize the product, the mixture was concentrated to 25 ml and the mixture stirred. The product was obtained by filtering in the form of white crystals. Yield: 3.52 g (33%). $^1H$ NMR (300 MHz, DMSO) δ 7.58 (dd, J=8.3, 0.7 Hz, 1H), 7.35 (dd, J=8.3, 2.4 Hz, 1H), 7.31 (d, J=2.2 Hz, 1H), 5.34 (s, 2H), 3.84 (s, 3H).

6-Hydroxyisobenzofuran-1(3H)-on

Nitrogen atmosphere, 6-methoxyisobenzofuran-1(3H)-on (3.00 g, 18.09 mmol) was dissolved in anhydrous dichloromethane (100 ml). The resulting mixture was magnetically stirred and cooled in an ice bath for 10 minutes. Then $BBr_3$ (3.46 ml, 36.18 mmol) was added. The reaction mixture was then heated to room temperature and stirred for 12 hours. Then 5 ml water was added and the mixture was transferred to a separating funnel and extracted with ethyl acetate (3×100 ml). The combined organic extracts were dried over magnesium sulphate, filtered and concentrated under reduced pressure, wherein a white solid was obtained. Yield: 1.52 g (56%). $^1H$ NMR (300 MHz, DMSO) δ 10.08 (s, 1H), 7.47 (dd, J=8.3, 0.6 Hz, 1H), 7.19 (d, J=2.3 Hz, 1H), 7.16 (d, J=2.3 Hz, 1H), 7.10 (d, J=2.0 Hz, 1H), 5.28 (s, 2H); ESI-MS: (calculated (MH)+: 151.04 g/mol, found: 151.05 m/z).

5-azido-2-(hydroxymethyl)benzohydrazide

Dissolve 6-hydroxyisobenzofuran-1(3H)-on (0.43 g, 2.83 mmol) in 6 ml dimethylformamide (DMF) and add hydrazine hydrate (1.42 ml, 28.26 mmol) and stir the solution at 100° C. for 3 hours. The DMF and hydrazine hydrate were removed under vacuum. The residue was purified by column chromatography ($CH_2Cl_2/MeOH$, 9:1), wherein a light yellow powder was obtained. Yield: 0.10 g (17%). Rf ($CH_2C12/MeOH$, 9:1) 0.40; $^1H$ NMR (300 MHz, DMSO) δ 10.08 (s, 1H), 9.73 (s, 1H), 7.47 (d, J=8.3 Hz, 1H), 7.18 (dd, J=8.3, 2.3 Hz, 1H), 7.10 (d, J=2.3 Hz, 1H), 4.57 (d, J=5.7

Hz, 2H), 4.50 (s, 2H), 3.33 (s, 2H), ESI-MS: (calculated (MH)+: 183.08 g/mol, found: 183.15 m/z).

Exemplary Purification with Capture Molecule (14)

The purification was performed with another peptide example 14 (AKADEVSLHKWYG; SEQ ID NO: 10) and a linker of formula (14) (Fängermolekül 14) on commercially available, aldehyde-modified agarose (High Density Glyoxal, 6BCT from ABT).

Solid Phase Peptide Synthesis and Purification

The automated solid phase peptide synthesis was performed in 100 µmol batches with a MultiPep RS peptide synthesis machine from Intavis AG. The synthesis was performed on a Wang-resin (1.0-1.4 mmol/g) from Carl Roth. Before the beginning of the synthesis, the corresponding amount of peptide synthesis resin was weighed in 5 mL syringe reactors (PE reactor from Intavis) and soaked in DMF. The weight of equivalents of amino acid was refers to the initial loading of the resin used, unless otherwise stated.

Fmoc-Removal:

To remove the temporary Fmoc protecting groups, the resin was treated once for 5 min and once more for 8 min with 1500 L piperidine/DMF (4:1) and subsequently washed seven times with 10.2 mL DMF and it was continued with the coupling of the Fmoc amino acid derivatives.

Coupling of Fmoc Amino Acid Derivatives:

A solution of 5 eq. amino acid in DMF (0.3 M) was pre-activated for 1 min at room temperature with solutions of 4.5 eq. HCTU in DMF (0.3 M) and 10 eq. NMM in DMF (0.6 M) and then added to the resin. After 30 min reaction time, the resin was washed three times with 10.2 mL DMF and it was continued with blocking the truncated sequences.

Blocking the Truncated Sequences:

The resin was treated twice for 5 min with 1.5 mL $AC_2O$/2,6-lutidine/DMF solution (5:6:89) and subsequently washed seven times with 10.2 mL DMF each.

Last Step Coupling of the Capture Molecule:

As the last step of the solid phase peptide synthesis, the capture molecule (14) was coupled to the desired target peptide (50 µmol). The synthesis resin was mixed with a solution of 4 eq. capture molecule (0.3 M), 6 eq. HOBt in DMF (0.4 M) and 4 eq. DIPEA in DMF (0.3 M) mixed. After a reaction time of 60 min, it was washed twice with 2 mL DMF each, twice with 2 mL $CH_2Cl_2$ and then washed again twice with 2 mL DMF.

Alternative Last Step of Acetylation of the Full-Length Peptide:

Analogously to the protocol for blocking the truncated sequences, the full-length peptide as a control sample was also acetylated (peptide acetylated).

Release from Polymeric Support:

The resin was treated with 3 mL of a solution of 95% TFA, 2.5% water and 2.5% triisopropylsilane. The synthesis resin was mixed with this cleaving mixture and shaken for 3 h at room temperature. Afterwards, the cleaving solution was collected and the resin was washed twice with 1 mL TFA each. The cleaving solution was combined with the washing solutions and concentrated by argon flow to approx. 1 mL volume. Afterwards, it was precipitated with 10 mL cold diethyl ether and the precipitate was centrifuged. The supernatant was discarded. In FIG. 4h (above) the chromatogram of the peptide without linker before purification is shown with a purity of 45%.

Purification

The crude precipitate (about 5 µmol theoretical yield) was dissolved in conjugation buffer (0.1 M $NH_4OAc$, 0.1 M aniline, pH=3.8). If the mixture did not dissolve completely, acetonitrile was added. In a 3 mL syringe reactor with a 25 µm PE prefilter 400 L (~160 mg) agarose were added. The purification resin was then conditioned by washing 3 times with conjugation buffer (0.1 M $NH_4OAc$, 0.05 M aniline, pH=3.8). The peptide solution was then added to the purification resin. Immobilization was then performed for 60 minutes. Afterwards, it was washed three times with conjugation buffer, three times with a 5 M urea solution, three times with 70% ethanol and finally five times with water. The mixture was then treated basically with 5 v % $NH_4OH$ in water to cleave conjugated peptide from the resin. Lyophilization provides the peptide as a white flaky solid.

Proof of Immobilization

To provide clear evidence of immobilization, acetylated peptide and peptide with bound linker were purified on modified as well as on pure agarose (6% B Agarose Bead STANDARD, ABT) with PEC in this experiment. The eluate after the left linker cleavage was assessed with UPLC-UV. The results showed that after cleavage, a significant signal of the product mass is only detected in peptide with bound linker on modified purification resin. In addition, it can be seen that also with pure agarose about 2.3% of the product is obtained compared to modified agarose.

TABLE 3

Integrals of the product peak for the peptides after purification with modified and unmodified agarose

|  | Peptide linker | | Peptide acetylated | |
| --- | --- | --- | --- | --- |
|  | Agarose | Modified agarose | Agarose | Modified agarose |
| Integral (µV * s) | 17759 | 763044 | 197 | 131 |
| Proportion | 2.31% | 100% | 0.03% | 0.02% |

Regeneration of the Purification Resin

After peptide purification with the capture molecule (14), the original aldehyde function of 1 remains blocked with the hydroxyl-modified capture molecule. To make the purification resin available for a new purification cycle, the resin must be regenerated and thus the aldehyde function restored. This is achieved by shifting the equilibrium by adding aldehydes or ketones. Regeneration for repeated purification cycles was demonstrated as follows:

Two purifications of peptide 14 were performed simultaneously (purification I). The purification resin was then washed four times each with a mixture of water, acetone and TFA (ketone, 49.95:49.95:0.1), or water, acetaldehyde and TFA (aldehyde, 89.95:9.95:0.1) and five times with water for regeneration. Afterwards the purification including the conditioning was performed in the same way as described above. The regeneration and purification was performed three times (purification II-IV) and the lyophilized product was taken up in equal volumes of water, acetonitrile and TFA (69.9:29.9:1) and measured with UPLC-MS.

TABLE 4

Integrals of the product peak and percentage proportion for the peptides after purification with modified agarose (purification I) and after three regeneration cycles (purification II-IV).

| Purification | Ketone Integral (µV * s) | Proportion | Purity | Aldehyde Integral (µV * s) | Proportion | Purity |
|---|---|---|---|---|---|---|
| I | 4100144 | 100% | 58.9% | 2138955 | 100% | 58.2% |
| II | 2044538 | 50% | 58.5% | 911365 | 43% | 58.7% |
| III | 1719147 | 42% | 57.8% | 567140 | 27% | 58.6% |
| IV | 381717 | 9% | 61.5% | 576371 | 27% | 59.8% |

The results showed that the resin can be regenerated in both cases. Regeneration with a ketone only decreases significantly in the third cycle (purification IV). In contrast, in aldehyde regeneration, the purification capacity remains at about a quarter of the initial capacity, but decreases to this value already after the second cycle (purification III). In both experiments a purity of about 60% was achieved, which remains constant during the regeneration cycles (example chromatogram for purification I, aldehyde, FIG. 4h (below)).

The invention claimed is:

1. Compound of the formula

X$_1$-L-X$_2$(1), wherein

X$_1$ is selected from

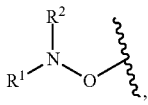
(2)

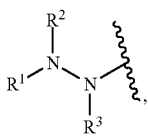
(3)

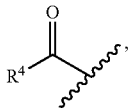
(4)

wherein each R$^1$ and R$^2$ is independently from each other selected from H or B, wherein at least R$^1$ or R$^2$ is B, wherein R$^3$ is selected from H or B,
  wherein B is an acid labile amine protecting group, wherein R$^4$ is selected from H, C$_1$-C$_{12}$-alkyl or aryl, wherein the aldehyde or keto group may be protected by an acid labile protecting group, L is selected from functional linkers, that are cleavable nucleophilically from X$_2$ under basic conditions, and are of the form -T-U-, wherein T is a spacer between X$_1$ and U, and wherein U is the cleavage activating part of the functional linker, wherein the activating part is formed to stabilize an anion formed during a basic cleavage from X$_2$, X$_2$ is of the form —Y—Z, wherein Y is selected from —O—C(=O)— or —S(=O)$_2$—, and Z is an electron-withdrawing leaving group.

2. Compound according to claim 1, wherein -B is selected from Boc (—C=OOtBu), trityl (—C(Ph)$_3$), Mmt (—C(Ph)$_2$C$_6$H$_4$OMe), DMT (—C(Ph)(C$_6$H$_4$OMe)$_2$), Cbz (—C=OOCH$_2$Ph), benzylideneamine (=CPh), phtalimides (=(CO)$_2$C$_6$H$_4$), p-toluenesulfonamides (—SO$_2$C$_6$H$_4$Me), benzylamine (—CH$_2$Ph), acetamides (—COMe), trifluoroacetamide (—COCF$_3$), Dde (1-(4,4-dimethyl-2,6-dioxocyclohex-1-ylidene)-3-ethyl) and 1-(4,4-dimethyl-2,6-dioxocyclohex-1-ylidene)-3-methylbutyl (ivDde), and/or the acetal- or ketal protecting groups are selected from

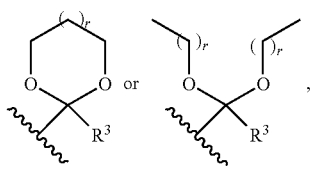

wherein r is 0 to 12.

3. Compound according to claim 1, wherein T is selected from —C$_1$-C$_{12}$—alkyl-, —R$^5$—C(=O)—NH—R$^6$—, —R$^5$—C(=O)—O—R$^6$—, —R$^5$—C(=O)—O—, —C(=O)—O—R$^6$—, —C(=O)—NH—R$^6$—, —C(=O)—, —C(=O)—O—, wherein R$^5$ and R$^6$ are independently from each other selected C$_1$-C$_6$-alkyls.

4. Compound according to claim 1, wherein U of the moiety T-U-Y is selected from the moieties according to the formulas (5), (6), (7), (8), (9), (10) and (11),

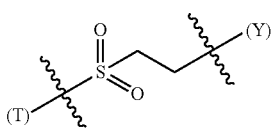
(5)

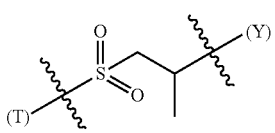
(6)

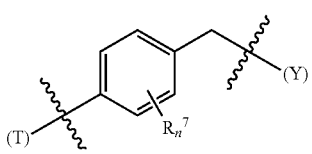
(7)

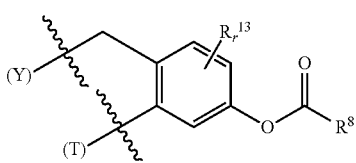
(8)

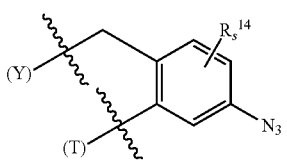
(9)

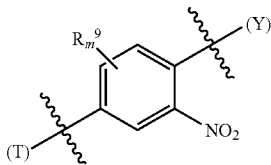
(10)

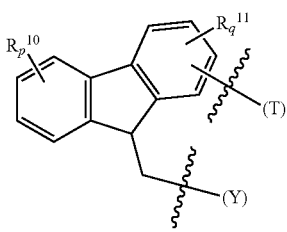
(11)

wherein R$^8$ is selected from C$_1$-C$_6$-alkyl, CF$_3$, CH$_2$CF$_3$,

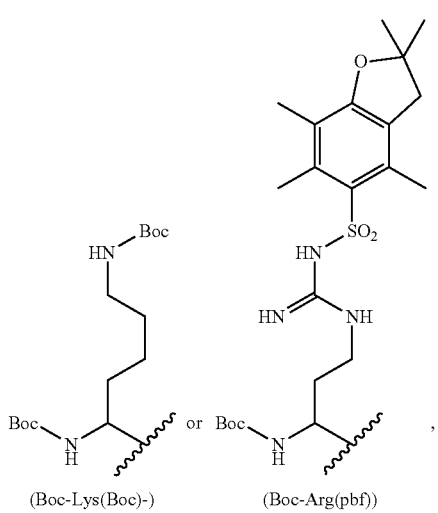

wherein $R^7_n$, $R^9_m$, $R^{10}_p$, $R^{11}_q$, $R^{13}_r$ and $R^{14}_s$ is selected from $C_1$-$C_6$-alkyl or —I and/or -M-effects generating substituents, wherein n equals 0, 1, 2, 3 or 4,
wherein m equals 0, 1, 2 or 3,
wherein p equals 0, 1, 2, 3 or 4,
wherein q equals 0, 1, 2 or 3,
wherein r equals 0, 1, 2 or 3,
wherein s equals 0, 1, 2 or 3.

5. Compound according to claim 1, wherein Z is selected from the group —F, —Cl, —Br, —I, —$N_3$, —$SR^{12}$, —$OCF_3$, —$OCH_2CF_3$, —$OSO_2CF_3$, —$SO_2C_6H_4CH_3$, —$SO_2CF_3$, —$SO_2CH_3$

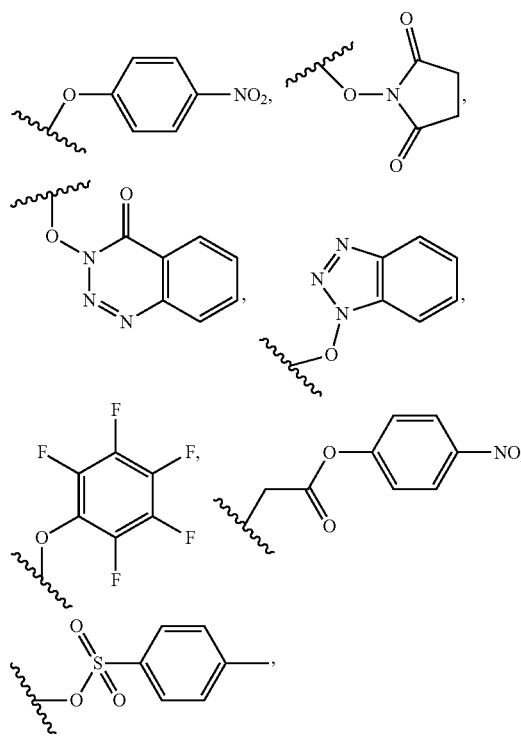

wherein $R^{12}$ is a $C_1$-$C_6$-alkyl-, an aryl- or a benzyl residue.

6. Compound according to claim 1, wherein X is a moiety of formula (2) or (3), wherein $R^3$ is H, $R^1$ and $R^2$ comprise a Boc protecting group or $R^1$ is H and $R^2$ is a Boc protecting group.

7. Compound according to claim 1, wherein Y is of the form —O—C(=O)—.

8. Compound according to claim 1,
wherein T is of the form —($CH_2$)—C(=O)—NH—($CH_2$)$_2$—, —($CH_2$)—C(=O)—O—($CH_2$)$_2$—, —C(=O)—O—($CH_2$)$_2$—,
wherein U is a moiety of formula (5) or (6),

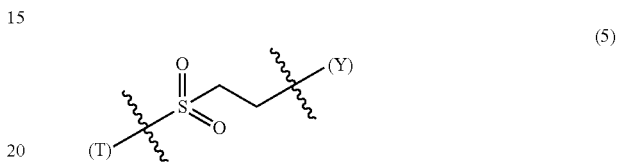

(5)

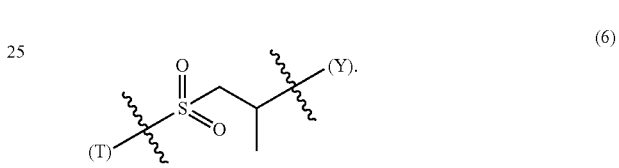

(6)

9. Compound according to claim 1,
wherein T is of the form —$CH_2$—C(=O)—O—, —C(=O)—O—, in particular —$CH_2$—C(=O)—O—,

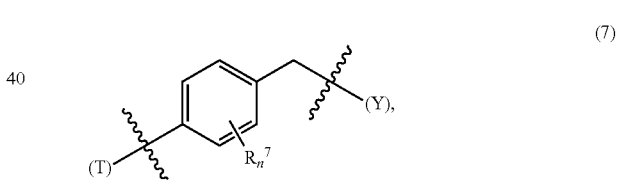

(7)

wherein U is a moiety of formula (7), wherein $R^7$ is selected from $C_1$-$C_6$-alkyl or —I and/or -M-effect generating substituents, in particular $C_1$-$C_3$-alkyl, —F, —Cl, —Br, —I, —CN —$NO_2$, —$N_3$, —$CF_3$, —$SO_3H$, —$CO_2H$ wherein n equals 0, 1, 2, 3 or 4, in particular 0 or 1, in particular 0.

10. Compound according to claim 1,
wherein T is of the form —$CH_2$-,
wherein U is a moiety of formula (8),

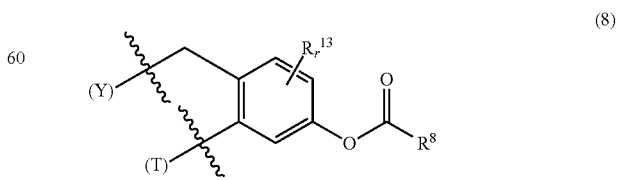

(8)

wherein $R^8$ is Boc-Lys(Boc) and r equals 0.

11. Compound according to claim 1,
wherein T is of the form —$CH_2$,(C=O),
wherein U is a moiety of formula (9), wherein s equals 0,

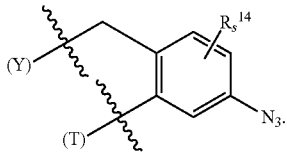
(9)

12. Compound according to claim 1,
wherein T is of the form —C(=O)—,
wherein U is a moiety of formula (10), wherein m equals 0,

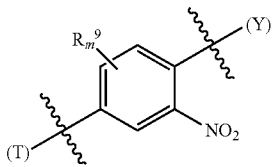
(10)

wherein Y is of the form —$SO_2$—, and
wherein Z is Cl.

13. The compound according to claim 1, wherein T is selected from substituted or unsubstituted —$C_1$-$C_{12}$-alkyl-, —$R^5$—C(=O)—NH—$R^6$—, —$R^5$—C(=O)—O—$R^6$—, —$R^5$—C(=O)—O—, —C(=O)—O—$R^6$—, —C(=O)—NH—$R^6$—, —C(=O), —C(=O)—O—, —$R^5$-phenyl-$R^6$—, —$R^5$-phenyl-, -phenyl-$R^6$—, and -phenyl-, wherein $R^5$ and $R^6$ are independently from each other selected substituted or unsubstituted $C_1$-$C_{12}$-alkyls.

14. The compound according to claim 4, wherein $R^7_n$, $R^9_m$, $R^{10}_p$, $R^{11}_q$, $R^{13}_r$, and $R^{14}_s$ are selected from $C_1$-$C_3$-alkyls, —F, —Cl, —Br, —I, —CN —$NO_2$, —$N_3$, —$CF_3$, —$SO_3H$, and —$CO_2H$.

* * * * *